United States Patent
Richelsoph et al.

(10) Patent No.: US 7,291,173 B2
(45) Date of Patent: *Nov. 6, 2007

(54) ARTIFICIAL INTERVERTEBRAL DISC

(75) Inventors: Marc Richelsoph, Bartlett, TN (US); Joseph Clift, Bartlett, TN (US)

(73) Assignee: Aesculap II, Inc., Center Valley, PA (US)

( * ) Notice: Subject to any disclaimer, the term of this patent is extended or adjusted under 35 U.S.C. 154(b) by 568 days.

This patent is subject to a terminal disclaimer.

(21) Appl. No.: 10/700,748

(22) Filed: Nov. 3, 2003

(65) Prior Publication Data

US 2004/0225364 A1 Nov. 11, 2004

Related U.S. Application Data

(63) Continuation-in-part of application No. 10/653,540, filed on Sep. 2, 2003, which is a continuation-in-part of application No. 10/430,861, filed on May 6, 2003.

(51) Int. Cl.
*A61F 2/44* (2006.01)
*A61F 2/30* (2006.01)

(52) U.S. Cl. .................................................. 623/17.13

(58) Field of Classification Search .. 623/17.11–17.16; 606/61
See application file for complete search history.

(56) References Cited

U.S. PATENT DOCUMENTS

| | | | |
|---|---|---|---|
| 4,759,769 A | 7/1988 | Hedman et al. | |
| 4,848,555 A | 7/1989 | Riese et al. | |
| 5,037,438 A | 8/1991 | Davidson | |
| 5,192,327 A | 3/1993 | Brantigan | |
| 5,258,031 A | 11/1993 | Salib et al. | |
| 5,314,477 A | 5/1994 | Marnay | |
| 5,401,269 A | 3/1995 | Büttner-Janz et al. | |
| 5,507,816 A | 4/1996 | Bullivant | |
| 5,545,227 A | 8/1996 | Davidson et al. | |
| 5,562,738 A | 10/1996 | Boyd et al. | |
| 5,676,701 A | 10/1997 | Yuan et al. | |
| 5,782,832 A | 7/1998 | Larsen et al. | |

(Continued)

FOREIGN PATENT DOCUMENTS

DE 2 263 842 12/1972

(Continued)

OTHER PUBLICATIONS

Partial European Search Report; Aug. 22, 2005; Berlin.

*Primary Examiner*—Pedro Philogene
(74) *Attorney, Agent, or Firm*—RatnerPrestia

(57) ABSTRACT

An artificial intervertebral disc including housing members including spaced inner surfaces facing each other and oppositely facing outer surfaces for engaging spaced apart intervertebral surfaces; self-adjusting bearing mechanisms operatively disposed between the inner surfaces for moving relative to the housing members to adjust and compensate for vertebral disc motion; and positioning ring for controlling motion and position of the bearing mechanisms and for absorption of compressive loads. An artificial intervertebral disc including housing members having an oval recess on the inner surfaces; oval bearing mechanisms operatively disposed within the oval recess between the inner surfaces for moving relative to the housing members to adjust and compensate for vertebral disc motion; and oval positioning ring. A spring member for an artificial intervertebral disc including a substantially annular body having an axially extended bore therethrough defining a passageway.

16 Claims, 45 Drawing Sheets

U.S. PATENT DOCUMENTS

| | | |
|---|---|---|
| 5,865,846 A | 2/1999 | Bryan et al. |
| 5,888,226 A | 3/1999 | Rogozinski |
| 5,893,889 A | 4/1999 | Harrington |
| 6,001,130 A | 12/1999 | Bryan et al. |
| 6,013,103 A | 1/2000 | Kaufman et al. |
| 6,063,121 A | 5/2000 | Xavier et al. |
| 6,146,421 A * | 11/2000 | Gordon et al. ............ 623/17.15 |
| 6,277,149 B1 | 8/2001 | Boyle et al. |
| 6,368,350 B1 | 4/2002 | Erickson et al. |
| 6,443,987 B1 | 9/2002 | Bryan |
| 6,491,726 B2 | 12/2002 | Pappas |
| 6,494,915 B1 | 12/2002 | Villar Gonzalez et al. |
| 6,517,580 B1 | 2/2003 | Ramadan et al. |
| 6,520,996 B1 | 2/2003 | Manasas et al. |
| 6,530,955 B2 | 3/2003 | Boyle et al. |
| 6,572,653 B1 | 6/2003 | Simonson |
| 6,582,466 B1 | 6/2003 | Gauchet |
| 6,645,248 B2 * | 11/2003 | Casutt ..................... 623/17.12 |
| 6,682,562 B2 * | 1/2004 | Viart et al. .............. 623/17.14 |
| 6,733,532 B1 * | 5/2004 | Gauchet et al. .......... 623/17.12 |
| 6,936,071 B1 * | 8/2005 | Marnay et al. .......... 623/17.15 |
| 6,984,245 B2 | 1/2006 | McGahan et al. |
| 7,001,432 B2 | 2/2006 | Keller et al. |
| 7,156,876 B2 | 1/2007 | Moumene et al. |
| 7,179,294 B2 | 2/2007 | Eisermann et al. |
| 2002/0035400 A1 | 3/2002 | Bryan et al. |
| 2003/0055427 A1* | 3/2003 | Graf ........................... 606/61 |
| 2003/0069640 A1 | 4/2003 | Ferreira et al. |
| 2003/0191534 A1 | 10/2003 | Viart et al. |
| 2004/0002761 A1 | 1/2004 | Rogers et al. |
| 2004/0034420 A1 | 2/2004 | Errico et al. |
| 2004/0133278 A1 | 7/2004 | Marino et al. |
| 2005/0033438 A1 | 2/2005 | Schultz et al. |
| 2005/0043803 A1 | 2/2005 | Schultz et al. |

FOREIGN PATENT DOCUMENTS

| | | |
|---|---|---|
| DE | G 90 00 094.3 | 1/1990 |
| DE | 90 00 094.3 | 3/1991 |
| DE | 691 02 369 | 1/1995 |
| DE | 299 11 422 | 9/1999 |
| DE | 203 10 432 | 9/2003 |
| DE | 203 13 183 | 11/2003 |
| EP | 0282 161 A1 | 2/1988 |
| EP | 0 560 141 | 9/1993 |
| EP | 94/04100 | 3/1994 |
| EP | 0 747 025 | 12/1996 |
| EP | 1 057 462 | 12/2000 |
| EP | 1 103 237 A2 | 5/2001 |
| EP | 0 955 021 | 9/2001 |
| EP | 1 103 237 A3 | 4/2002 |
| EP | 1 250 898 | 10/2002 |
| EP | 1 344 508 | 9/2003 |
| EP | 1 374 808 | 1/2004 |
| EP | 1 421 922 | 5/2004 |
| EP | 1 188 423 | 9/2004 |
| EP | 1 263 352 | 12/2004 |
| FR | 2 694 882 | 2/1994 |
| FR | 2 799 638 A1 | 10/1999 |
| FR | 2 718 635 | 1/2001 |
| WO | WO 00/04851 | 2/0000 |
| WO | WO99/05995 | 2/1999 |
| WO | WO 00/13619 | 3/2000 |
| WO | WO 00/35385 | 6/2000 |
| WO | WO 00/01893 A1 | 1/2001 |
| WO | WO 01/01893 | 1/2001 |
| WO | WO 01/68003 | 9/2001 |
| WO | WO 03/084449 | 10/2003 |
| WO | WO 03/090648 | 11/2003 |
| WO | WO 03/094806 A1 | 11/2003 |

* cited by examiner

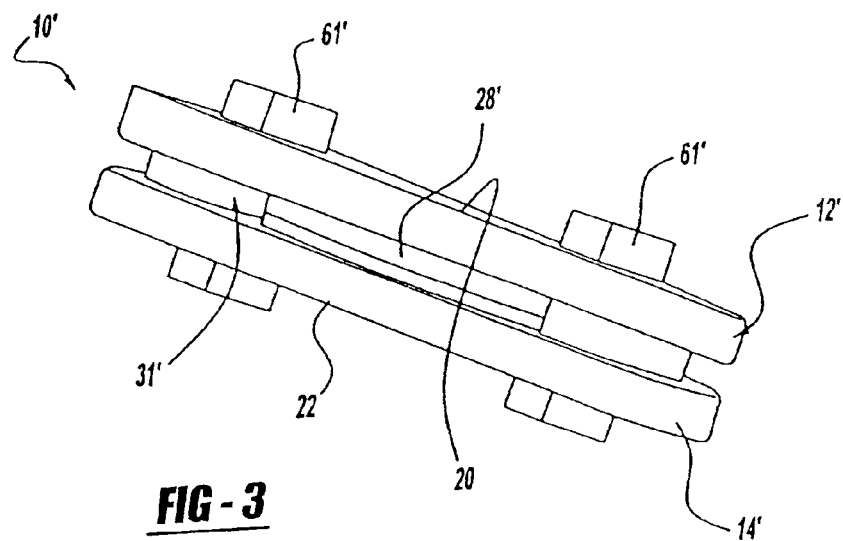
FIG-3
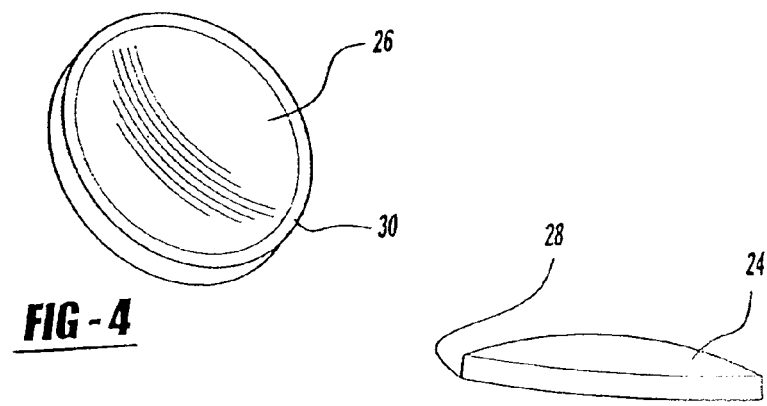
FIG-4
FIG-5

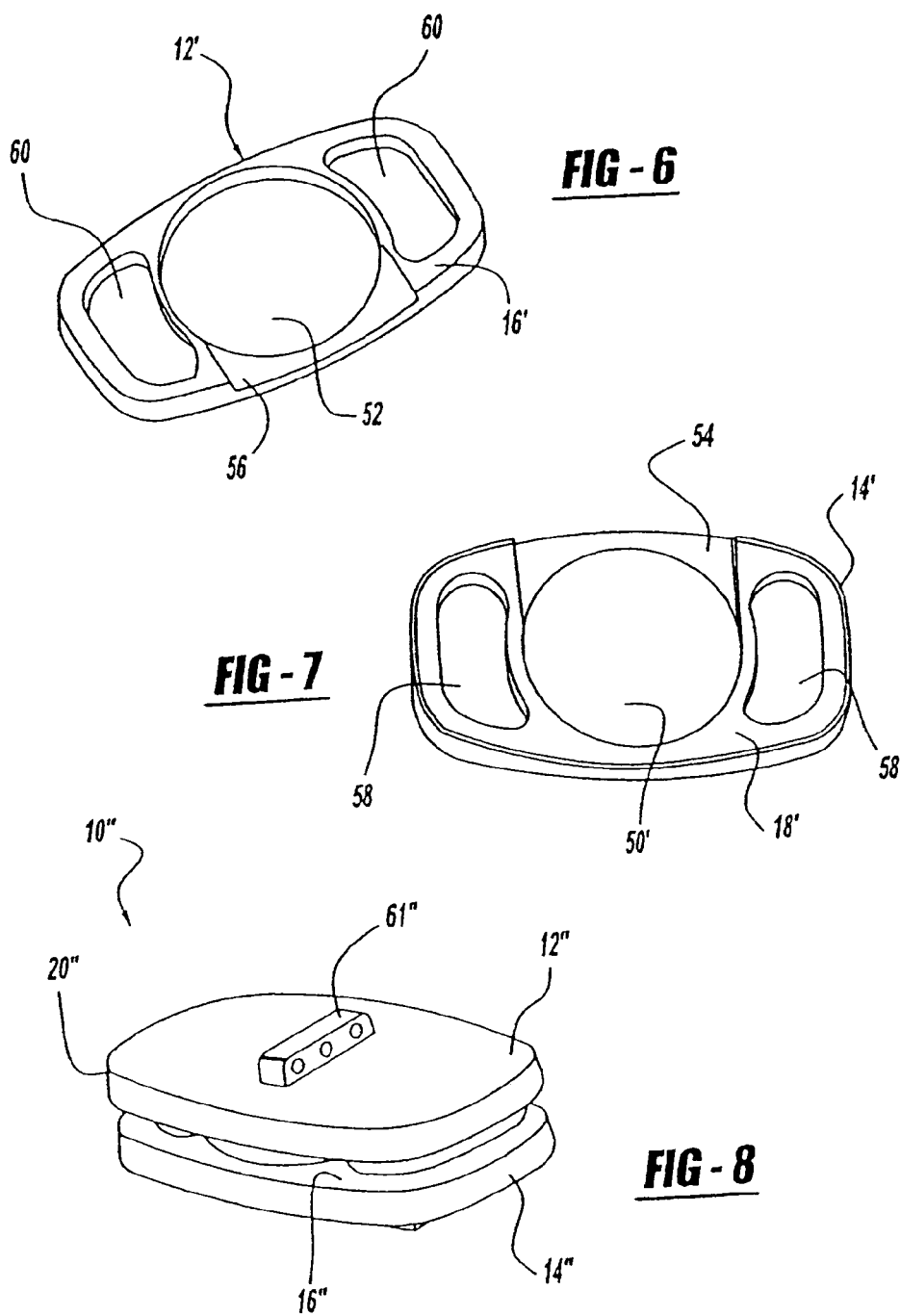

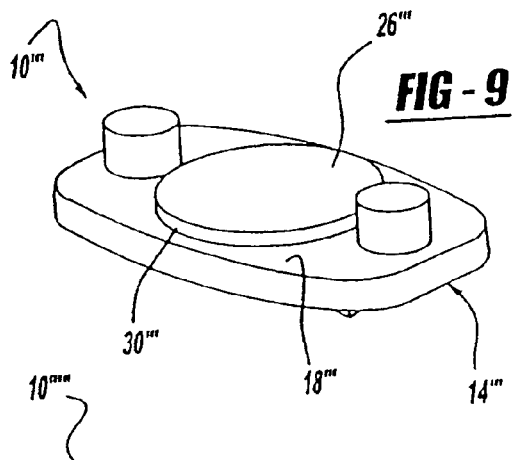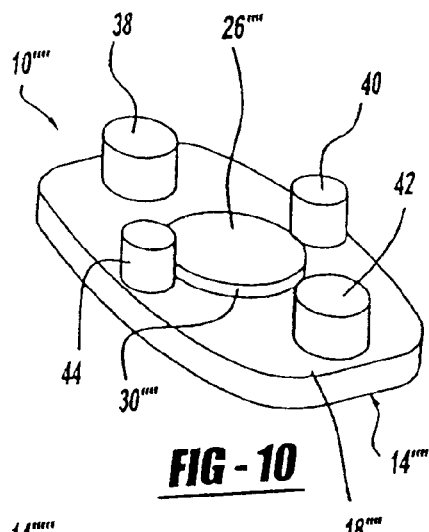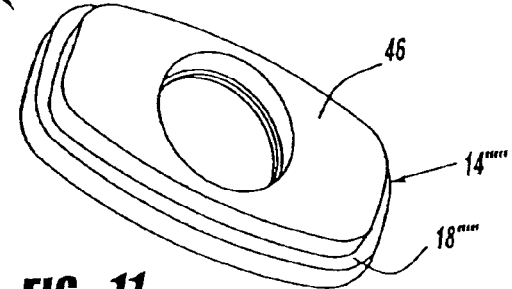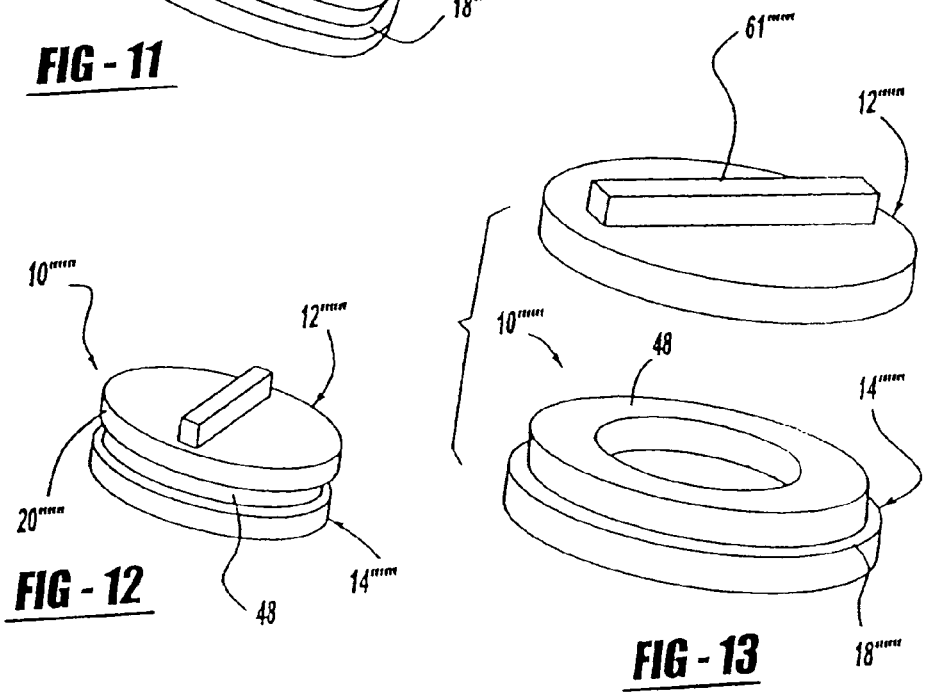

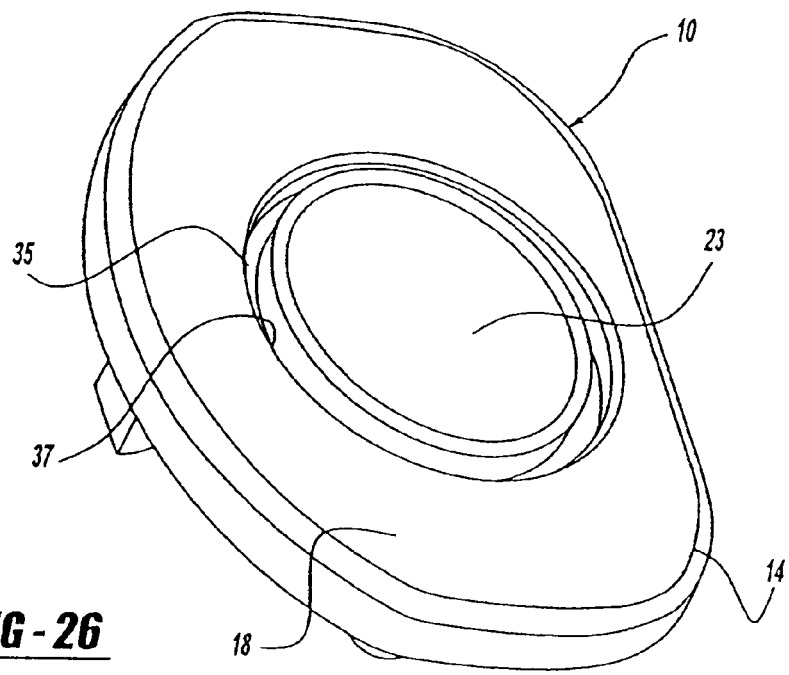
FIG - 26
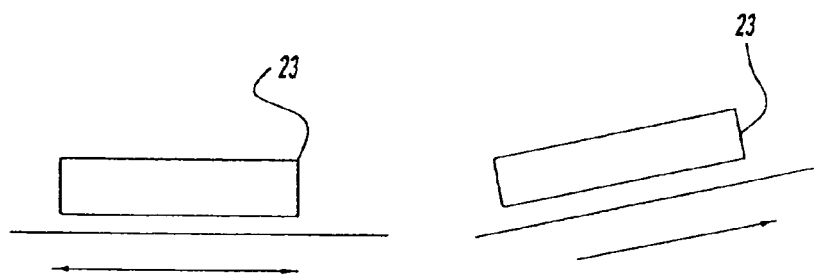
FIG - 27a  FIG - 27b

ARTIFICIAL INTERVERTEBRAL DISC

CROSS REFERENCE TO RELATED APPLICATIONS

This patent application is a Continuation-In-Part application of U.S. patent application Ser. No. 10/653,540, filed Sep. 2, 2003, which is a Continuation-In-Part application of U.S. patent application Ser. No. 10/430,861, filed May 6, 2003, which are incorporated herein by reference in their entirety.

BACKGROUND OF THE INVENTION

1. Technical Field

The present invention relates generally to a spinal implant assembly for implantation into the intervertebral space between adjacent vertebral bones to provide stabilization and continued postoperative flexibility and proper anatomical motion. More specifically, the present invention relates to an artificial intervertebral disc, sometimes referred to as an intervertebral spacer device, for functioning as a load sharing and bearing device for replacement of the damaged, decayed, or otherwise nonfunctioning intervertebral disc.

2. Background of the Invention

The spine is a complex structure consisting of multiple flexible levels. Each level consists of a system of joints defined by adjacent vertebral bones. The system of joints includes intervertebral discs, which are a two-part structure. The disc consists of a nucleus and an annulus. The system allows motion while the facet joints add posterior stabilization to the spinal column. The disc allows motion and cushioning to the joint.

The complex system of the joint is subjected to varying loads and problems over time, including disc degeneration due to a variety of reasons. Disc degeneration can be attributed to aging, damage due to excessive loading, trauma, and other anatomical issues. Facet joints of the structure can be compromised due to the same reasons, as well as due to arthritic changes. Severe joint degeneration and failure can often cause sufficient pain to require surgical intervention.

The current standard method of treatment for severe pain caused by spine joint problems is fusion at the damaged level of the spine. The treatment, when successful, fuses the damaged section into a single mass of bone. The fusion of the joint eliminates motion of the joint, thereby reducing or eliminating pain at that level. Success rates for pain elimination are very high for this method of treatment. However, since the entire spine works as a system, fusion results in complications.

Elimination of motion at the spine alters the biomechanics of the spine at every other level. If one level is fused, then loads are absorbed by one less disc into a system not designed for such change. Thus, the remaining discs must redistribute loads, each disc absorbing a greater load. In addition, the spine flexes to absorb loads. A fusion alters the means by which the spine flexes, which also increases the loads on the remaining healthy discs. In turn, it is well understood that a complication of fusion is that additional fusions may be required in the future as the other discs deteriorate due to the altered biomechanics of the spine. In other words, short-term pain relief is exchanged for long-term alterations of the spine, which, in turn, usually require further surgery.

There are numerous prior art patents addressing the issue of disc replacement. The U.S. Pat. Nos. 6,443,987 B1 and 6,001,130, both to Bryan, disclose polymer composite structures for cushioning intervertebral loads. The U.S. Pat. Nos. 5,258,031 to Salib, et al. and 5,314,477 to Marnay disclose ball and socket type implants addressing the issue of intervertebral mobility. These patents are exemplary of a first approach using an elastomer as a motion and dampening structure and a second approach utilizing a ball and socket joint to create a moving pivot joint. There are many variations on these concepts, which include mechanical springs and more complex structural mechanisms. A significant portion of the prior art addresses the issues of intervertebral motion but do not address anatomical loading considerations.

The current state of prior art artificial intervertebral discs are associated with various problems. For example, a number of implants constructed from polymers are of insufficient strength to work effectively in the higher loading areas, such as the lumbar spine. Such polymers often take compressive sets so that the original height of the implant decreases over time. A surgeon must either compensate for the compression by initially using a larger polymer prosthesis and estimate compression or use the appropriately sized polymer prosthesis and later surgically replace the same once the irreversible compression of the prosthesis is unacceptable.

Implants constructed with ball and socket joints severely restrict or eliminate shock cushioning effect of a normal disc. This implant can provide motion, but biomechanically, the ball and socket joint negatively affects other healthy discs of the spine. The result can be long-term problems at other levels of the spine, as seen with the current treatment of fusion.

Other implants, not discussed above, utilize bearing surfaces usually having polyethylene bearing against metal interfaces. Polyethylene as a bearing surface is problematic in large joint replacement due to the wear properties of the material. Since artificial discs are intended to be implanted over long periods of time, such wear can be highly damaging to surrounding tissue and bone.

In view of the above, it is desirable to provide a solution to intervertebral disc replacement that restores motion to the damaged natural disc area while allowing for motion as well as cushioning and dampening, similar to the naturally occurring disc. In addition, it is preferable to allow such motion, cushioning, and dampening while preventing a polymer or elastomeric material from experiencing the relatively high compressive loads seen in the spine. It is also preferable to allow a bearing surface to share the spinal loads with the polymer and elastomeric material. Finally, it is preferable to control changes to the artificial motion intraoperatively to adjust for anatomical conditions.

SUMMARY OF THE INVENTION

According to the present invention, there is provided an artificial intervertebral disc including housing members having spaced inner surfaces facing each other and oppositely facing outer surfaces for engaging spaced apart intervertebral surfaces; self-adjusting bearing mechanisms operatively disposed between the inner surfaces for moving relative to the housing members to adjust and compensate for vertebral disc motion; and positioning ring for controlling motion and position of the bearing mechanisms and for absorption of compressive loads. Also provided is an artificial intervertebral disc including housing members having spaced inner surfaces facing each other and oppositely facing outer surfaces for engaging spaced apart intervertebral surfaces, wherein the inner surfaces include an oval recess thereon;

oval bearing mechanisms operatively disposed within the oval recess between the inner surfaces for moving relative to the housing members to adjust and compensate for vertebral disc motion; and oval positioning ring operatively engaged with the oval recess and oval bearing mechanisms for controlling motion and position of the bearing mechanisms and for absorption of compressive loads between the bearing mechanisms and the housing members. The present invention further provides a spring member for an artificial intervertebral disc including a substantially annular body having an axially extended bore therethrough defining a passageway.

DESCRIPTION OF DRAWINGS

Other advantages of the present invention can be readily appreciated as the same becomes better understood by reference to the following detailed description when considered in connection with the accompanying drawings wherein:

FIG. 3 is a side perspective view of a second embodiment of the present invention;

FIG. 4 is a perspective view of a lower disc constructed in accordance with the present invention;

FIG. 5 is a side view of an upper disc constructed in accordance with the present invention;

FIG. 6 is a top perspective view of an upper housing member made in accordance with the present invention;

FIG. 7 is a top plan view of a lower housing member made in accordance with the present invention;

FIG. 8 is a side perspective view of a third embodiment of the present invention;

FIG. 9 is a perspective view of the present invention with the top housing member removed;

FIG. 10 is a perspective view of an alternative pad configuration of the present invention;

FIG. 11 is a perspective view of a further alternative embodiment of the pad member;

FIG. 12 is a further alternative embodiment of the present invention;

FIG. 13 is an exploded side perspective view of the embodiment shown in FIG. 12;

FIG. 26 is a top view of the multidirectional mobile bearing of the present invention;

FIGS. 27A and B are side views of the mobile bearing of the present invention;

DETAILED DESCRIPTION OF THE INVENTION

Figure 1:
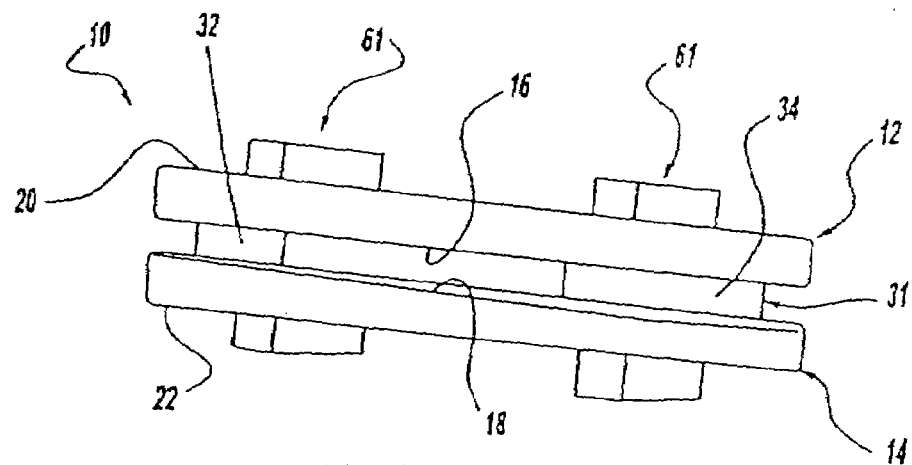
FIG. 1 is a side perspective view of a preferred embodiment of the present invention.

An artificial intervertebral disc constructed in accordance with the present invention is generally shown at 10 in the Figures. Similar structures of various embodiments are indicated by primed numerals in the Figures. The invention is an artificial intervertebral disc, sometimes referred to by other terminology in the prior art such as intervertebral spacer device, or spinal disc for replacement of a damaged disc in the spine. The invention restores motion to the damaged natural disc that allows for motion as well as cushioning and dampening. As described below in more detail, the present invention also allows changes to the artificial disc motion intraoperatively to adjust for specific anatomical conditions.

Referring to the Figures, the disc 10 includes an upper housing member generally shown at 12 and a lower housing member generally shown at 14. The housing members 12, 14 include spaced inner surfaces 16 and 18 facing each other and oppositely facing outer surfaces 20, 22 for engaging spaced apart vertebral surfaces. A pair of bearing surfaces 24, 26 extend from each of the inner surfaces 16, 18 for engaging each other while allowing for low friction and compression resistant movement of the housing members 12, 14 relative to each other while under compression. As shown in the various Figures, the bearing surfaces are integral with disc members 28, 30. The housing members 12, 14 can be made from various materials including metals, such as titanium, as well as ceramics, and plastics. Additionally, the housing members 12, 14 can be coated with materials to reduce friction between the components of the disc 10, specifically between the housing members 12, 14 and bearing disc members 28, 30. Coating materials include, but are not limited to, TiN (Titanium Nitride), diamond, diamond-like materials, synthetic carbon-based materials, chromium-based materials, and any other similar coating materials known to those of skill in the art. If integral with the bearing surfaces 24, 26, the housing members 12, 14 can be made from the preferred material for the bearing discs 28, 30 as discussed above. Based on this teaching, various other configurations can be made by those skilled in the art incorporating the present invention.

The bearing surfaces 24, 26 preferably form a mobile bearing 23 that is capable of automatically adjusting the position of the bearing 23 within a housing 14 as needed. The mobile bearing 23 is shown in FIGS. 24 through 29. The bearing 23 is preferably made of any material that slides along the surface of the housing 14 in which it is placed, with minimal to no wear, on either the bearing 23 or the housing 14. Examples of such materials include ceramic, metal, or other suitable materials that do not negatively react with the housing 14.

The bearing 23 of the present invention is disposed within a slot 35 of a housing 14. The bearing 23 is able to freely move or float within the slot 35 in response to movement of the housing 14. The bearing 23 is designed to provide proper cushioning and support of the housing 14 as is required by the specific system in which the bearing 23 is placed. The bearing 23 can be used in any joint for providing proper support of the joint. For example, if the bearing 23 is used in an artificial intervertebral disc assembly, the bearing 23 provides cushioning so as to prevent the plates that are housing the disc from touching and wearing on one another. When the bearing 23 is utilized within the knee, the bearing also provides cushioning for the housing 14 during movement of the housing 14.

The bearing 23 disclosed herein can move freely under load conditions while maximizing the contact area of the upper and lower bearing surfaces 20, 24. In other words, within the slot 35 that the bearing 23 is disposed, the bearing 23 can move in any direction necessary to provide the proper support for the housing 14. The bearing 23 is able to move in this manner because the bearing 23 is a floating bearing, thus it is not attached or affixed to the housing 14 in which it is placed. Instead the bearing 23 "floats" within the housing 14, thus enabling the bearing 23 to be mobile and free to move in any direction necessary to provide proper support.

The housing 14 limits the "floating" motion of the bearing 23. In other words the movement of the bearing 23 can be limited based upon the size of the housing 14 and more specifically the slot 35 in which the bearing 23 is disposed. The slot 35 in which the bearing 23 is disposed dictates the range of movement of the bearing 23, i.e. movement can be constrained such that the bearing 23 can only move from an anterior to a posterior position. More specifically, the slot includes side walls 37, which define the size and shape of the slot 35, and a seat 39 on which the bearing is disposed. The movement of the bearing 23 is restricted based upon the shape of the walls 35 of the slot 35 in which the bearing 23 sits. For example, the slot 35 can be in the shape of a circle, an oval, or any other round-sided shape. The slot 35 must be shaped to have rounded sides so as to prevent the bearing 23 from lodging in a corner of the slot 35. The slot 35 can be formed such that the seat 39 does not have a uniform depth, such that there are peaks or angles within the slot 35, as shown in FIG. 27. The lack of uniformity restricts movement of the bearing 23 within the slot 35 because the bearing 23 would require additional force in order to slide in the direction of the peak or angle.

Figure 28:
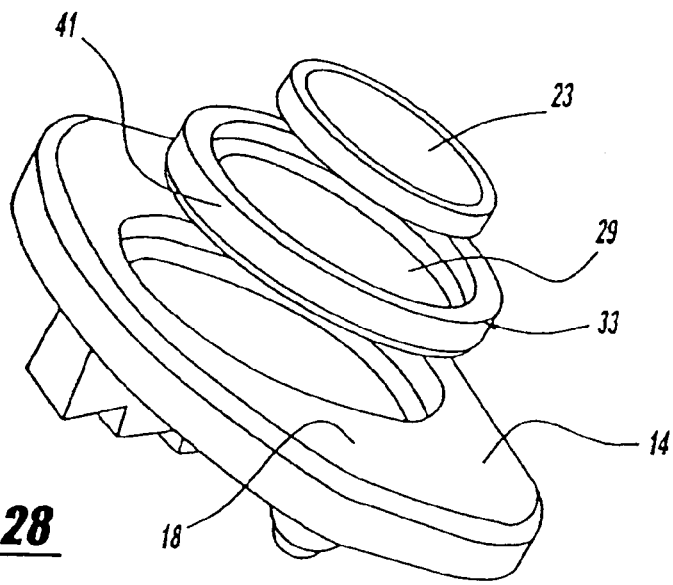
FIG. 28 is a side perspective view of the mobile bearing of the present invention resting in a seat.
Figure 29:
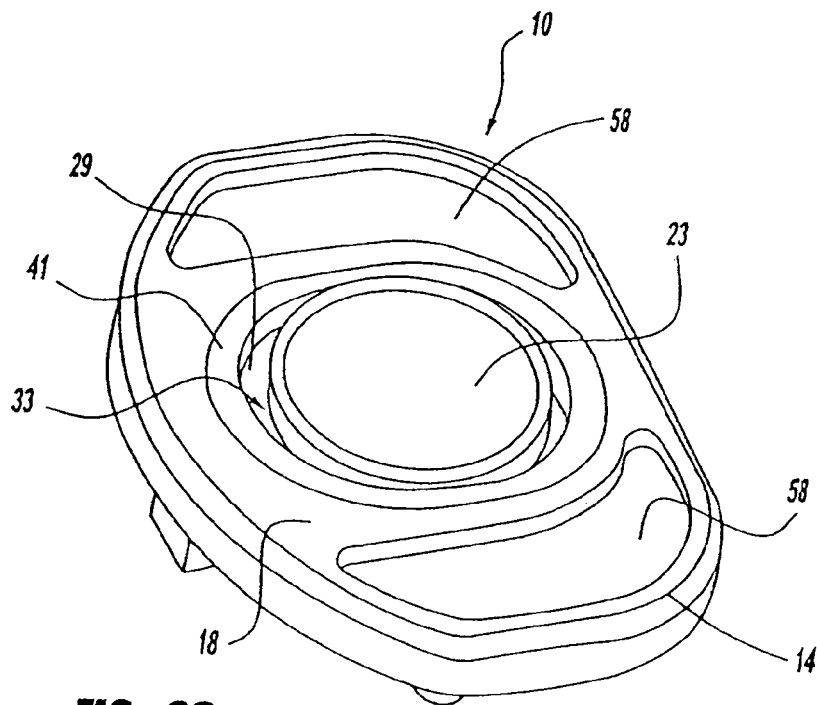
FIG. 29 is a top perspective view of the seat and bearing combination in a housing having recesses for load sharing pads.

A removable insert 33, as shown in FIGS. 28 and 29, can also be disposed within the housing 14 for holding the bearing 23 in place. The insert 33 includes an upper surface 29 for engaging the bearing surfaces 24, 26. The insert 33, can be made of any material that enables the bearing 23 to functionally "float" across the insert 33 without excessive friction. The benefit of including the insert 33 in a housing 14 is that the insert 33 can be made of a different material than that of the housing 14. Accordingly, the housing 14 can be made from a first composition that is advantageous for the functionality of the housing and provides other strength characteristics while the insert 33 can be made from a more lubricious material to allow for more efficient friction-free movement of the bearing 23 thereon.

The movement of the bearing 23 is restricted based upon the shape of the insert 33 into which the bearing 23 is placed. The insert 33 includes side walls 41, which define the size and shape of the insert 33, and an insert seat 29 on which the bearing is disposed. The movement of the bearing 23 is restricted based upon the shape of the walls 41 of the insert 33 in which the bearing 23 sits. For example, the insert 33 can be in the shape of a circle, an oval, or any other round-sided shape. The insert 33 must be shaped to have rounded sides so as to prevent the bearing 23 from lodging in a corner of the insert 33. The insert 33 can be formed such that the insert seat 29 does not have a uniform depth, such that there are peaks or angles within the insert 33, as shown in FIG. 27. The lack of uniformity restricts movement of the bearing 23 within the insert 33 because the bearing 23 would require additional force in order to slide in the direction of the peak or angle.

Figure 2:
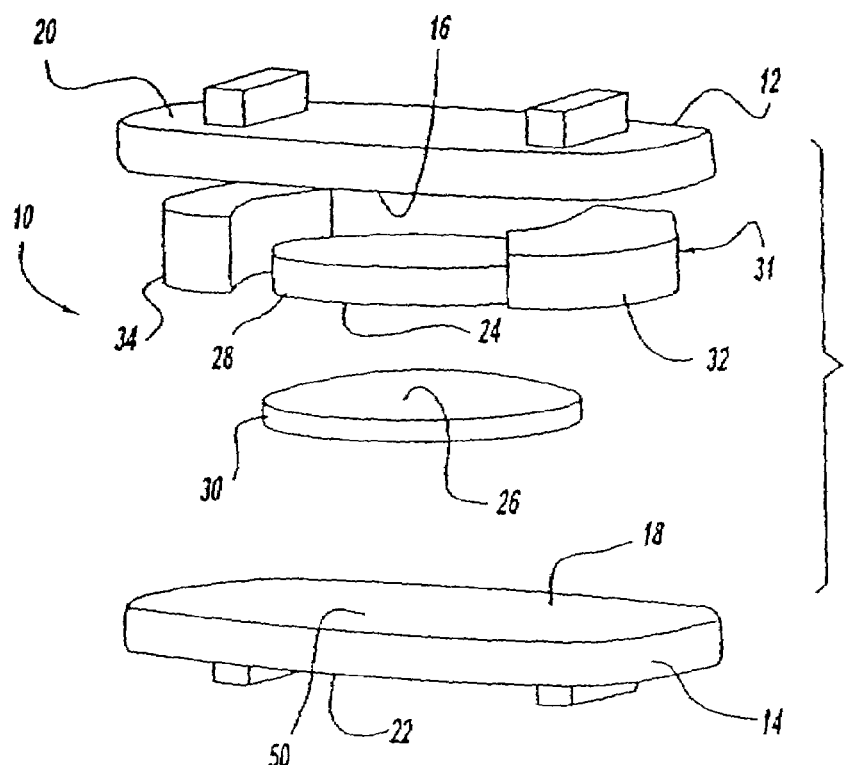
FIG. 2 is a side exploded view of the embodiment shown in FIG. 1.

The housing 14 can also include load distributing dampening and cushioning pad recesses 32, 58. Load sharing pads 32, 34 generally shown at 31 and specifically indicated as pads 32 and 34 in FIGS. 1 and 2 are disposed between the inner surfaces 16, 18 and about at least a portion of the bearing surfaces 24, 26 for sharing absorption of compressive loads with the bearing surfaces 24, 26 while limiting relative movement of the housing members 12, 14. More specifically, under in vivo loading conditions, the centralized bearing surfaces 24, 26 and the floating bearing surfaces not only provide for three-dimensional movement relatively between the housing members 12, 14, but also share with the load sharing pads 32, 34 the function of distributing compressive loads on the device 10 to provide a system for motion and effective load distribution. The centralized low friction and compression resistant bearing surfaces 24, 26 allow full motion in multiple planes of the spine while the load distributing damper and cushioning pads 32, 34 simultaneously share the load. Critical is the function of the pads 32, 34 sharing the load with the bearing surfaces 24, 26. Although the pads 32, 34 can be compressible, the compression is limited by the noncompressibility of the bearing surfaces 24, 26. Likewise, although the bearing surfaces allow for motion in multiple planes, the pads 32, 34 are fixedly secured to the housing members 12, 14, thereby allowing for a degree of flexibility and therefore movement of the housing members 12, 14 relative to each other, yet limiting such movement. In total, each element, the bearing surfaces 24, 26, and pads 32, 34, allow for movement, yet limit such movement, whether it is the sliding movement of the bearing surfaces 24, 26 or the cushioning movement allowed by the pads 32, 34. Each element allows for relative movement, yet each element limits the movement of the other element of the system.

In view of the above, the system allows restoration of normal motion while maintaining load cushioning capabilities of a healthy disc. This is particularly apparent with motion of the spine. Any rotation of the upper and lower housing members 12, 14 causes the load distributing dampening and cushioning pads 32, 34 to absorb some of the load.

As shown in the various Figures, the bearing surfaces 24, 26 can include a concave surface portion on one of the upper or lower disc members 28, 30, and a convex surface portion on the other. The concave surface is seated within the convex surface for sliding movement relative thereto effectively resulting in relative pivoting motion of the housing members 12, 14, which compresses at least a portion of the load sharing pads 32, 34 while extending at least a portion of the oppositely disposed load bearing pad 32, 34. Alternatively, either one of the top and bottom disc members 28, 30 can have either of the convex or concave surfaces.

The disc members 28, 30 can be made from a composition that is noncompressible. Such compositions can be selected from the group including ceramics, plastics, and metal bearing materials, such as cobalt and chrome. Alternatively, the housing members 12, 14 can include projections wherein the disc members 28, 30 are effectively integral with the housing members 12, 14. In this situation, the entire housing, including the projections having the bearing surfaces 24, 26 thereon, can be made from the noncompressible material, preferably a ceramic. As stated above, alternative configurations can be made by those skilled in the art once understanding the present invention.

The load sharing pads 32, 34 can be in various configurations shown in the Figures, such as paired pads 32, 34 shown in FIGS. 1–3. Alternatively, the device 10 can include four oppositely disposed pads 38, 40, 42, 44 as shown in FIG. 10. A further embodiment of the invention is shown in FIG. 11, wherein a single pad 46 substantially covers the surface 18'''' of the housing member 14''''. The pads can contour to the shape of the housing members such as shown in FIGS. 12, 13, wherein the pad member 48 is an annular pad member disposed with a annular housing 12'''''', 14''''''. The selection of such housing members 12, 14 and pad members 31 can be determined based on the location of the placement of the device 10 as well as the spacing conditions between the vertebrae and load bearing necessities depending on the level of the spine being addressed. In other words, different shaped devices, such as the round shaped housing members shown in FIG. 12 can be used for placement between smaller discs, such as cervical spines whereas more rectangular shapes, such as the housing members shown in FIGS. 1–11 can be used in between lumbar vertebrae.

The load sharing pads 31, in which ever shape they are configured, are elastic for allowing relative twisting movement between the housing members 12, 14 effecting relative three-dimensional movement between the housing members 12, 14, while limiting the movement and preventing contact between the housing members 12, 14 except for the contact between the bearing surfaces 24, 26. By elastic, it is meant that the pad members 31 are compressible and stretchable, yet provide a self-centering effect on the assembly with specific regard to the housing members 12, 14, as well as the bearing surfaces 24, 26. Deflection or rotation of the forces created due to relative movement of the bearing surfaces 24, 26, and likewise the housing members 12, 14, forces the pads 31 to act in such a way to counter the force, thus allowing a unique self-centering capability to the assembly 10. While in an ideal situation, wherein the patient's facets are uncompromised and ligamental balances are intact, this self-centering aspect may not be completely necessary. In other words, the patient's anatomy may still provide stabilization and specifically, ligaments may provide self-centering. However, ligamental imbalance, and damaged facets would normally make an artificial disc questionable, at best, with use of the current technology that is available. In such cases, having the ability to self-center and restrict motion (the pads 31 of the present invention are elastic and thus restrict motion by stretching and returning to rest), the possibility of extending indications to patients currently considered outside of the scope of artificial disc technology will be highly advantageous.

The pads 31 of the present invention provide further advantages to the invention. A key advantage is the ability to adjust the pads 31 to patient and surgeon requirements. In such cases wherein range of motion needs to be restricted due to compromised facets, a harder, less elastic pad can be inserted between the housing members 12, 14. Since this less elastic pad would move and stretch less, the disc would be automatically restricted in motion. This method of adjusting pads can be done intraoperatively to compensate for surgical and patient conditions. To one skilled in the art, one can fine-tune the assembly 10 to a patient and surgeon's needs with multiple pads of different properties or materials.

The pads 31 are made from a polymer or elastomer that allows deflection under load. Examples of such polymers and elastomers are silicone, polyurethane, and urethane composites. As discussed above with regard to flexibility or elasticity, the content and composition of the pads 31 are adjustable. A highly dense material creates a very rigid disc, while a very soft material creates a very free moving disc. The motion would be restricted in all planes of the pad depending upon these factors. Rotation is also restricted, as well as flexion or movement of the disc. The amount of compression possible is restricted or allowed according to the pads material properties. This is true of motion towards the back or side-to-side motion. Thus, the pads 31 are always in contact and always share the load, under any adjustment of relative positioning of the housing members 12, 14. Since motion forces the pads to be in contact, the pads 31 automatically damper loads imposed by the artificial disc construct 10.

With specific regard to the flexibility or elasticity of the polymer or elastomer composition of the pads 31, the pads can be selected from a composition having a durometer from 20 to 98 on the Shore OO Scale. Alternatively, the pads 31 can be selected from a composition having a durometer from 10 to 100 on the Shore A Scale. A further alternative is for the pads 31 to be selected from a composition having a durometer from 22 to 75 on the Shore D Scale. In any event, the pad members 31 can be selected during the operation and procedure by the clinician to suit a specific situation. Although the pad members 31 can be pre-inserted between the housing members 12, 14 prior to insertion of the device 10 in situ, the various configurations of the present invention can allow for in situ replacement of the pad members 31 so as to custom select the flexibility or elasticity of the members. In this manner, the pad members 31 are custom designed for the individual environment of the intervertebral space into which the device is being disposed.

The disc members 28 and 30, and pads 31 can be contained or locked in position in between the housing members 12, 14 by various means. The disc 28, 30 can be locked to the housing members 12, 14 by a press fit taper, retaining ring, or other means. The key aspect of such locking mechanisms is to prevent the disc members 28, 30 from moving against the upper or lower housing members 12, 14 once installed in order to prevent additional wear.

FIGS. 1 and 2 show disc members 28, 30 disposed in recesses (only the lower recess 50 is shown in FIG. 2 in an exploded view) in each of the inner surfaces 16, 18 of the housing members 12, 14. FIGS. 6 and 7 show plan views of a second embodiment of the housing member 12', 14', wherein each recess 50', 52 includes a ramped surface 54, 56 leading from an outer edge to the inwardly tapered recess portion 50', 52. The ramping 54, 56 allows access of the disc members 28,30 in between the housing members 12', 14' after placement of the housing members 12', 14' in the intervertebral space. This intraoperative access of the disc members 28, 30 allows the surgeon to test different size disc members under load conditions to perfectly fit the disc members in place. Such an advantage is not obtainable with any prior art device.

Figure 16:
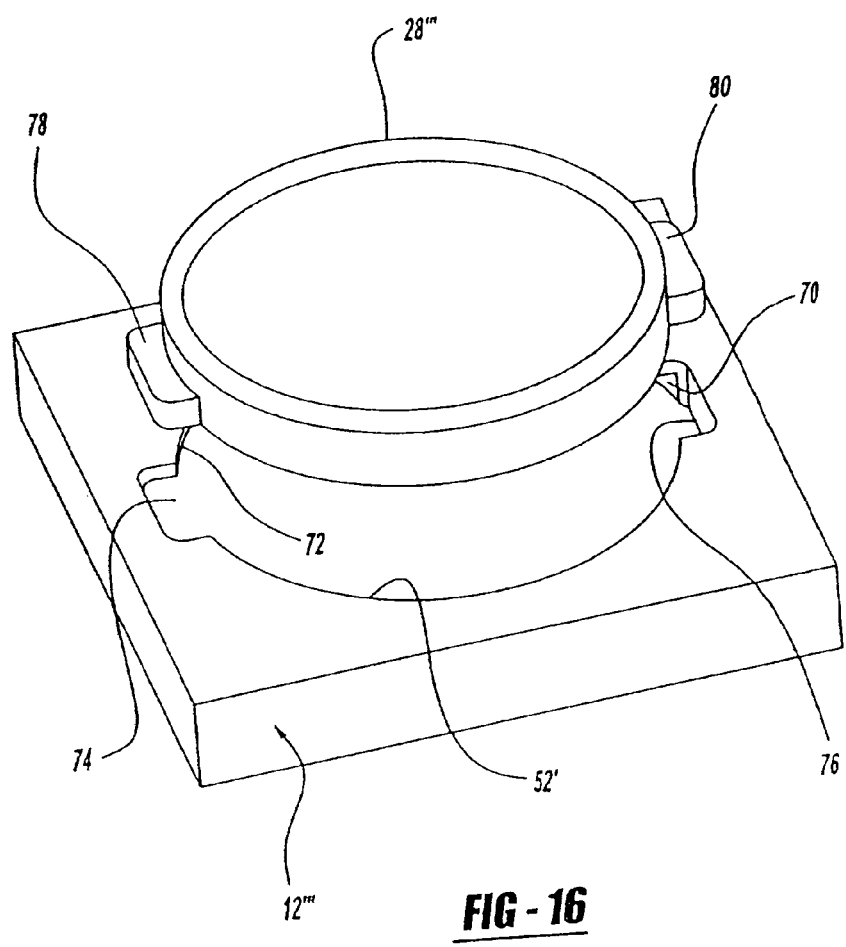
FIG. 16 is an exploded view of a further embodiment of the present invention demonstrating a bayonet type locking of a disc member to a housing member.
Figure 17:
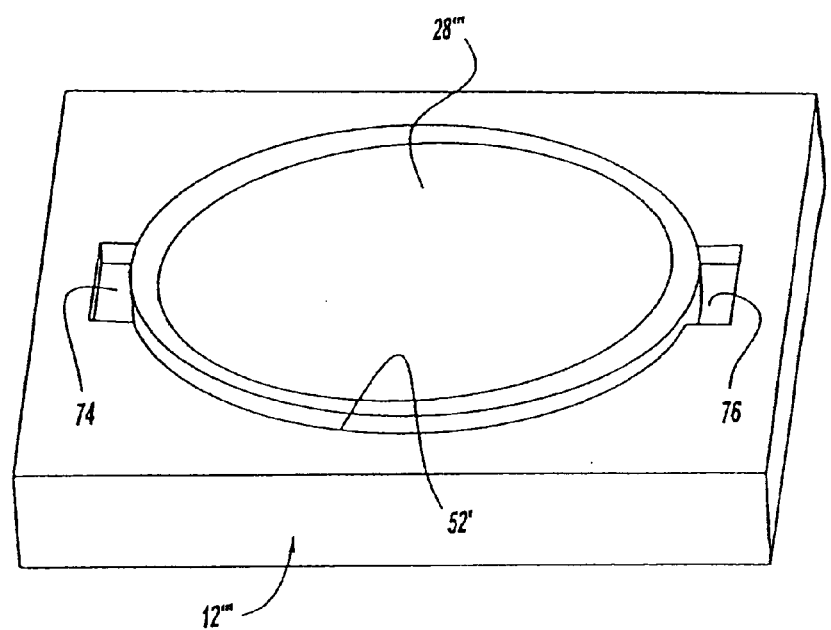
FIG. 17 is a perspective view of the disc member utilizing the bayonet locking mechanism to lock the disc member within a housing member.

An alternative mechanical mechanism for locking the disc members within the housing members is shown in FIG. 16. The representative housing member 12''' includes recess 52'. The recess 52' includes a substantially arcuate peripheral undergroove 70. The groove is defined by a lip portion 72 including at least one and preferably at least two openings 74, 76. The disc member 28''' includes bayonet style flanges 78, 80 extended radially outwardly therefrom, the flanges 78, 80 being shaped so as to be received through recess 74, 76. In operation the disc member 28''' can be disposed within the recess 52' such that the flanges 78, 80 align with recesses 74, 76. Once the disc member 28''' can be rotated thereby providing a bayonet style locking mechanism of the disc member 28''' within the housing 12''', as shown in FIG. 17.

Figure 18:
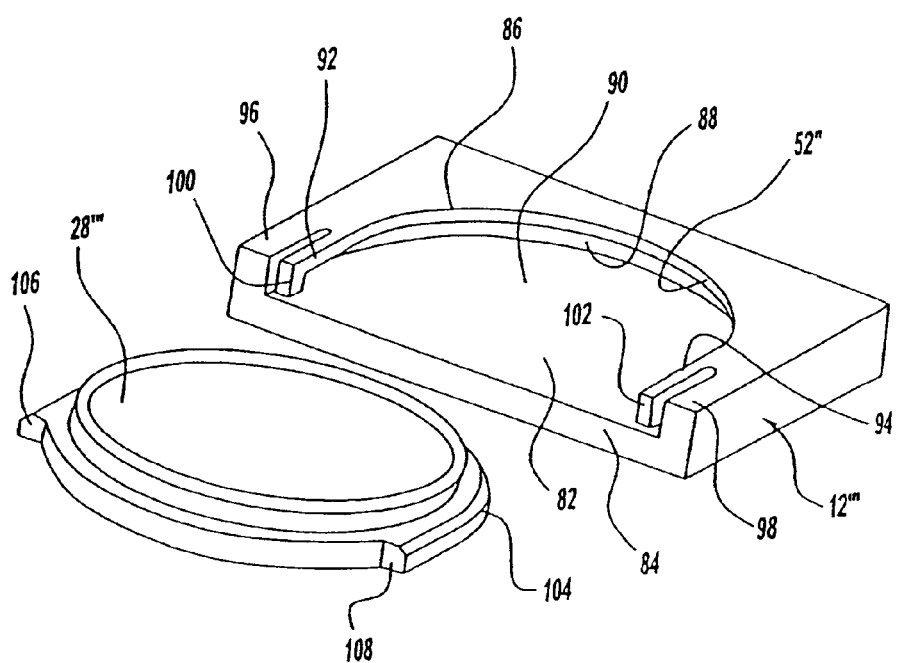
FIG. 18 is an exploded view of a disc member and housing member showing a further embodiment of a locking mechanism for locking the disc member within the housing member.
Figure 19:
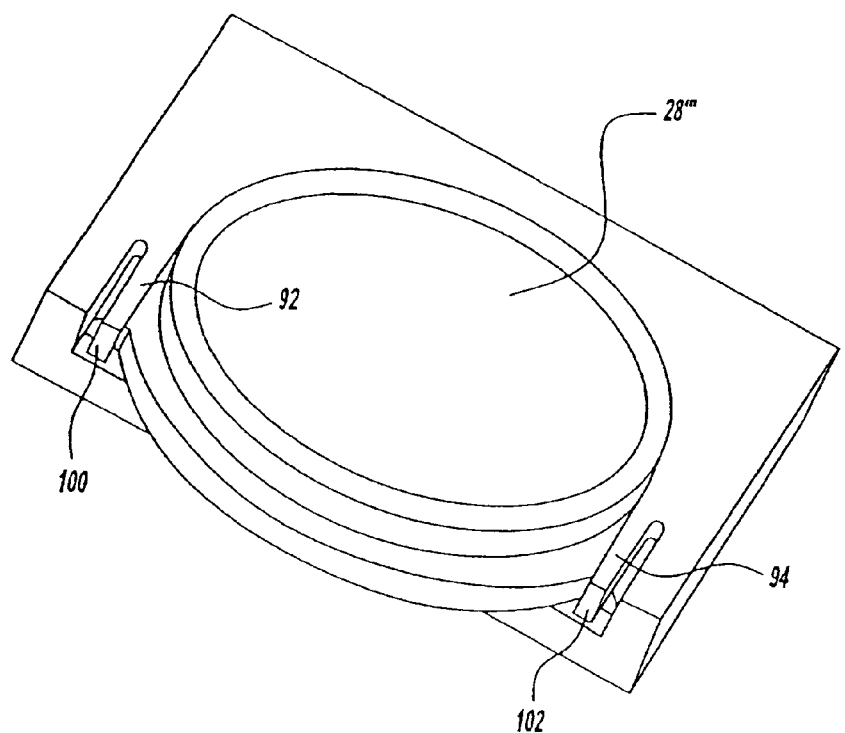
FIG. 19 is a perspective view showing the disc member locked within the housing member.

A further alternative embodiment of the locking mechanism is shown in FIGS. 18 and 19. The housing member 12''' includes a substantially arcuate recess 52'' having an open end portion 82 extending to an edge 84 of the housing member 12'''. The recess 52'' includes a lip portion 86 extending about a substantial portion thereof defining an inner groove 88 between the seating surface 90 of the recess 52'' and the lip portion 86. Arm portions 92, 94 are extensions of the lip portion 86 but extend from and are separate from peripheral ends 96, 98 of the housing member 12''' The arm portions 92, 94 have a spring-like quality such that they can be deflected outwardly from the arcuate circle defined by the recess 52''. Each of the arms 92, 94 has an elbow portion 100, 102 extending from each arm portion 92, 94 towards the seating surface 90, respectively. The disc member 28''' includes a substantially arcuate peripheral, radially outwardly extending flange portion 104. The flange portion 104 includes two abutment edges 106, 108. In operation, the flange 104 and disc member 28''' are disposed within the annular recess or groove 88, deflecting outwardly the arms 92, 94. Once disposed in the recess 52'', as shown in FIG. 19, the elbows 100, 102 engage the abutment surfaces 106, 108 of the disc member 28''' thereby locking the disc member 28''' in place. Outward deflection of the arms 92, 94 can selectively release the disc member 28''' from locked engagement to provide for further adjustment of the selection of the disc member during an operation procedure.

Also, as best shown in FIGS. 6 and 7, the pads members 31 can be disposed in recesses 58, 60 in the lower and upper housing members 12', 14' respectively. It is preferable to permanently adhere the pad members 31 to the housing members 12', 14' by use of mechanical mechanisms and/or various adhesives, such as cyanoarylates, urethanes, and other medical grade adhesives. This list of adhesives, as with other listings of ingredients in the present application, is merely exemplary and not meant to be exhaustive.

Examples of mechanical mechanisms for locking the pad members 31 into recesses in the housing members are shown in FIGS. 20–23. One such mechanism is an undercut locking mechanism shown in FIGS. 20–22. Housing member 12'''' includes a central recess 52 such as shown in FIG. 6 having a ramp portion 56. The ramp portion 56 includes a centrally located tongue groove 57 allowing for the insertion of a spatula type device under a disc member disposed within the recess 52 for releasing the disc member from the recess, similar to the use of a shoehorn type mechanism. Recesses 60' include undercut recesses 110, 112 for locking engagement with a peripheral flange portion 114 extending from an edge 116 of a pad member 31'. Since the pad member is made from a deflectable material, the flange portion 114 can be force-fit into and seated within the undercut 110, 112. The undercut locking mechanism effectively prevents the pad member 31' from disengagement with the housing member 12"" in situ. Of course, the upper flange 118 would be locked within a similar undercut locking detail of recesses within the opposing housing member (not shown).

Figure 23:
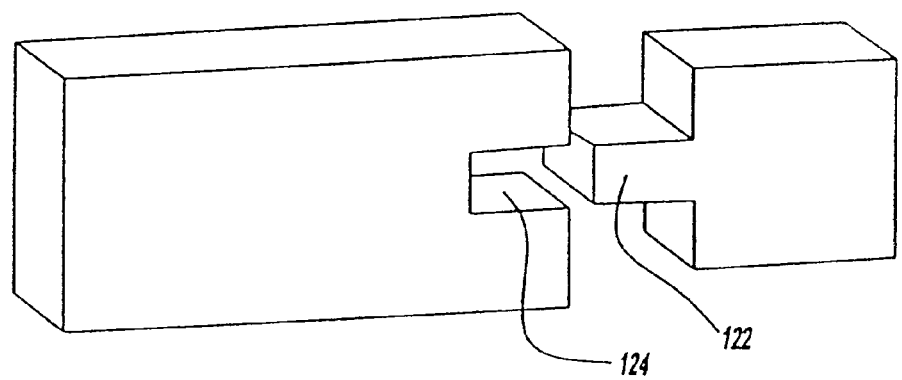
FIG. 23 shows a further embodiment of a locking mechanism made in accordance with the present invention.
Figure 24:
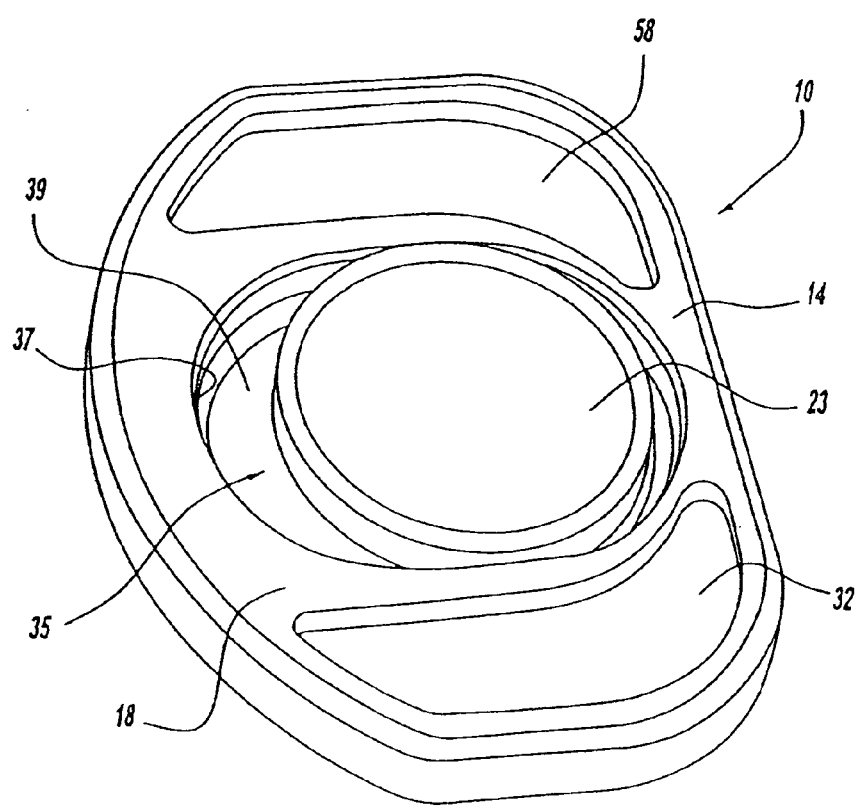
FIG. 24 is a top view of the mobile bearing of the present invention.
Figure 25:
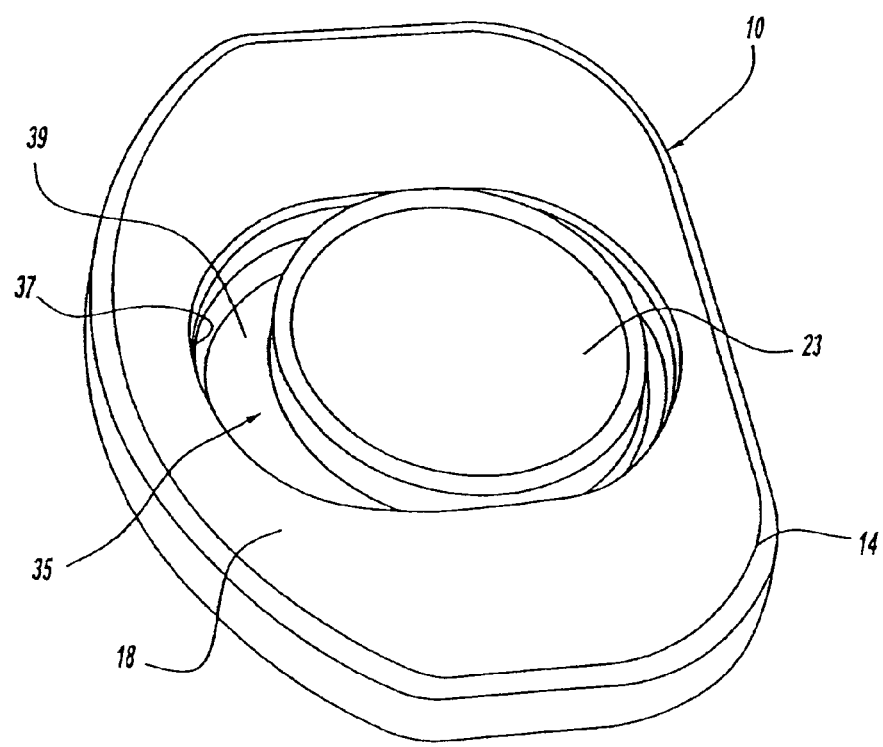
FIG. 25 is a top view of the artificial disc including a mobile bearing with no load sharing pads.

An alternative locking mechanism between the pad member and housing member can be a tongue-and-groove relationship as shown in FIG. 23. Either the pad or the housing can include the tongue portion 122 and the other pad and housing members can include the groove 124. In other words, either of the locking members can include the tongue 122 and the other of the members being locked would include the groove 124. An alternative of this or the other locking mechanism shown is that the recess and/or pad can include multiple grooves or slots as well as multiple tongues.

The various recesses or pockets 50', 52, 58, 60 can be of different relative sizes and shapes. For example, the upper housing member 12' may have a larger recess or pocket for seating a relatively larger one of said discs 28 and the lower housing member 14' may be include a smaller (larger and smaller referring to diameter of the annular recess) of the recesses or pockets for seating a relatively smaller one of the lower disc 30, thereby providing for an increased range of motion at the bearing surface interface.

Figure 14:
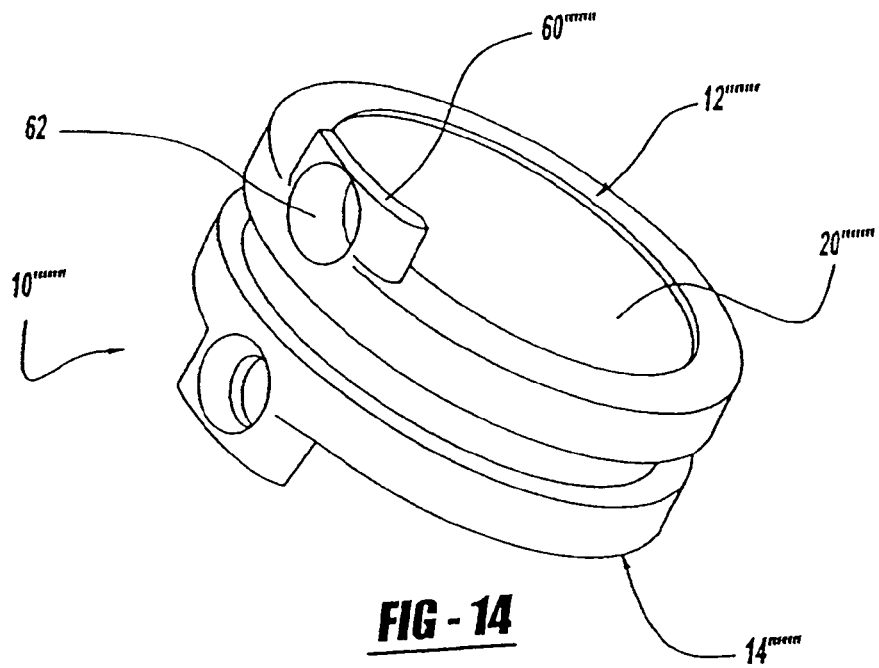
FIG. 14 shows an alternative embodiment of the housing members of the present invention.
Figure 15:
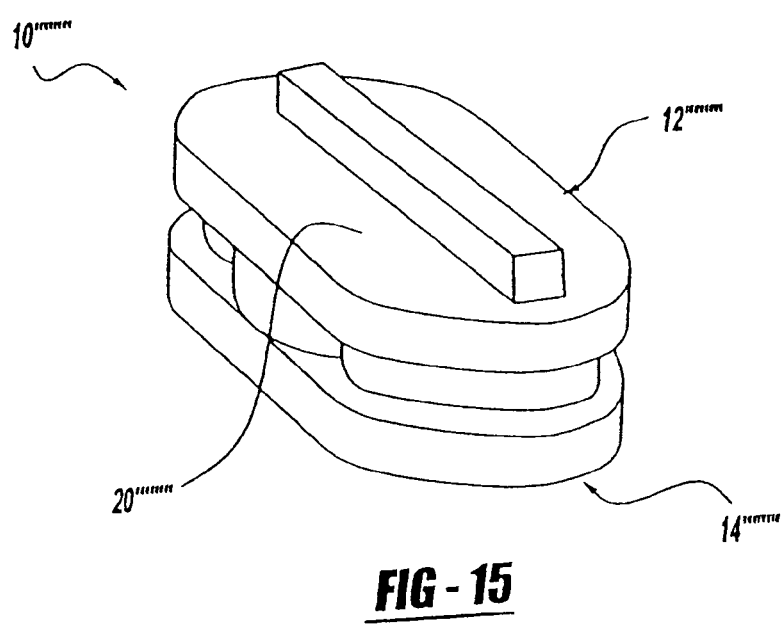
FIG. 15 shows a further alternative embodiment of the housing members of the present invention.

The various Figures show that the outer surfaces 20, 22 of the various embodiments of the housing members 12, 14 can include flanges generally indicated at 60. The flanges 60 or fins, as they are sometimes referred to in the art, provide a mechanism for fixation to the intervertebral surfaces. Various embodiments, such as those shown in FIGS. 1 and 2 are dual fin constructs. Other embodiments, such as those shown in FIGS. 8, 12, and 13 are single fin or single flange constructs. Depending upon the nature of the surfaces to which the outer surfaces 20, 22 are to abut, the surgeon can select various flange or fin configurations. Additionally, the fins 60 can be located in alternative positions, either centrally as shown in many of the Figures, or peripherally, as shown in FIG. 14, for a specific use with anterior extension plates, as with screw fixations. The flanges, such as flange 60"""" can include a bore 62 therethrough, which can be either a smooth surface or threaded depending on its intended use.

The outer surfaces 20, 22 can be smooth, which allows for easier revision as it allows for minimal to no ingrowth or they can be textured. Texturing of the outer surfaces 20, 22 allows ingrowth for long-term fixation of the assembly 10. Porous coatings, plasma spray, grit blasting, machining, chemical etching, or milling are examples of techniques for creating ingrowth capable surfaces. Coatings that enhance bone growth can also be applied. Examples of such coatings are hyroxyapatite and bone morphogenic proteins.

Figure 20:
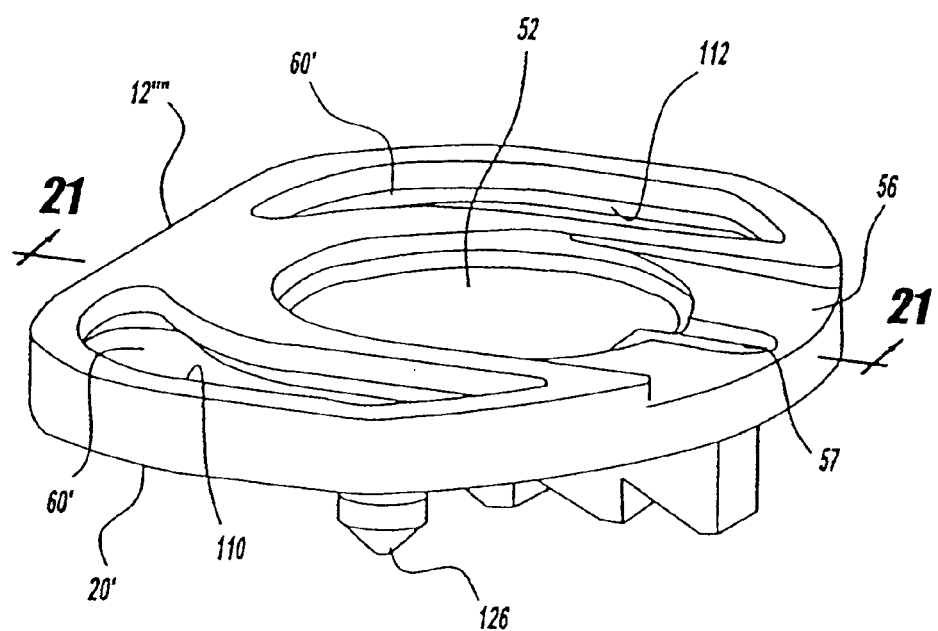
FIG. 20 is a perspective view of the a further embodiment of the housing member.
Figure 21:
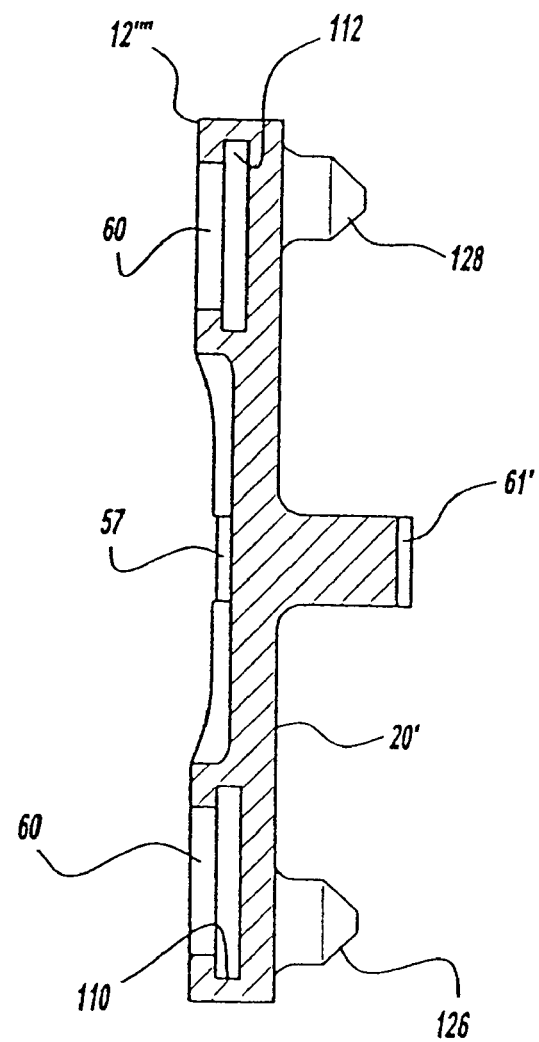
FIG. 21 is a cross sectional view taken along line 21—21 in FIG. 20.
Figure 22:
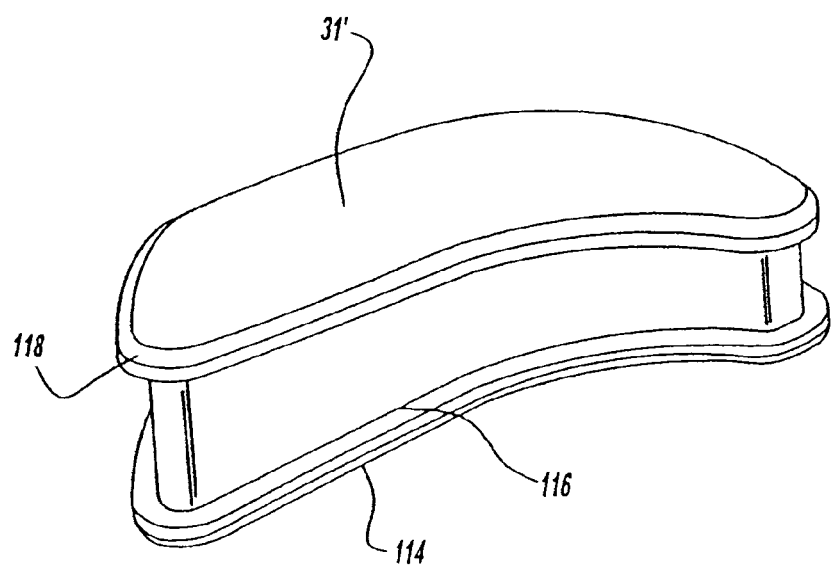
FIG. 22 is a perspective view of a load sharing pad member including flanges for locking engagement in the recesses of the housing member shown in FIGS. 20 and 21.

FIGS. 20 and 21 provide structure for further rotational stability of the device in situ. The housing member 12"" includes pointed portions 126, 128 extending from the outer surface 20' thereof. The point members 126, 128 function in conjunction with the flange portion 61' to engage an opposing vertebral surface. The point portions 126, 128 being disposed radially peripherally from the centrally disposed flange 61' provide at least a three-point engagement of the vertebral surface thereby preventing rotation of the housing member 12"" relative thereto. Of course, the point portions 126, 128 can be in made in various configurations and extend various amounts from the outer surface 20' to be custom suited to a specific vertebrae surface shape.

Figure 30:
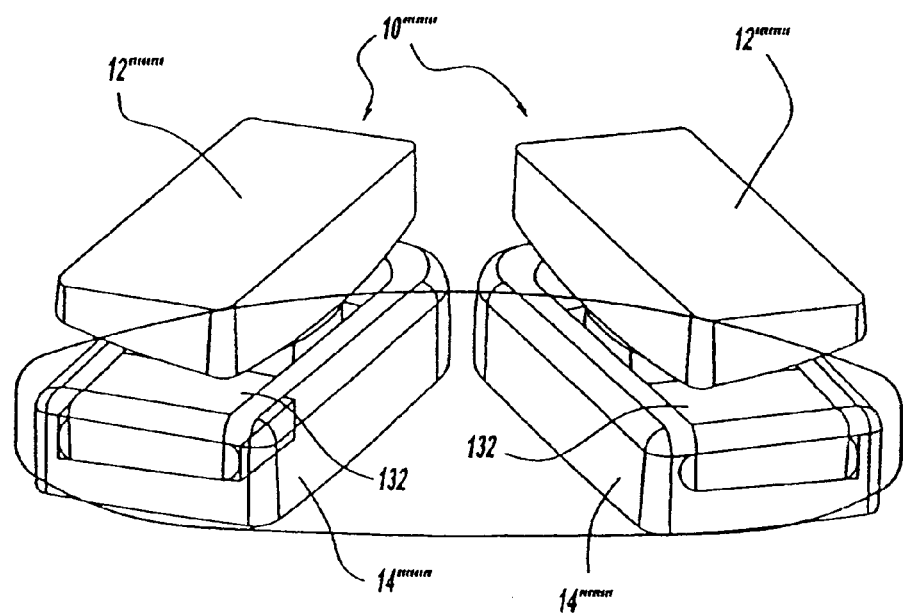
FIG. 30 is a side perspective view of a third embodiment of the present invention.
Figure 31:
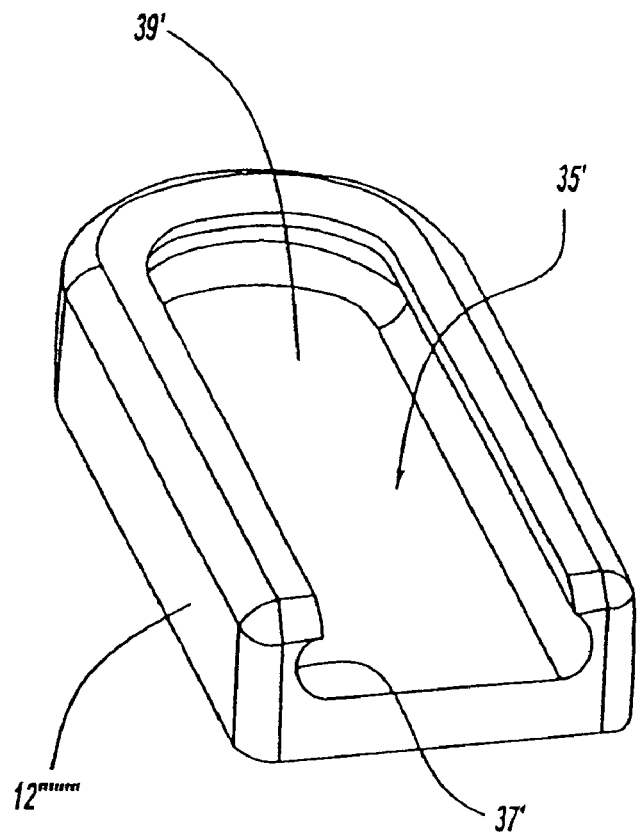
FIG. 31 is a perspective view of the base plate of a third embodiment of the present invention.

Alternatively, as shown in FIGS. 30–40, the disc 10"""" can be formed as two separate pieces that are inserted into an intervertebral space, generally shown as 146 in FIG. 30. The benefit of this formation of the disc 10"""" is that the discs 10"""" can be inserted during a posterior insertion. The two discs 10"""" function so that the units work in tandem and effectively become one artificial disc assembly. The arrangement of the two discs 10"""" enables each disc 10"""" to be inserted on either side of the spinal column into the intervertebral space 146 and work in conjunction as a single artificial disc assembly 10"""". The two discs 10"""" are angled toward the mid-line of the vertebral body 146. While two disc assemblies 10"""" are described herein, more than two discs 10"""" can also be utilized without departing from the spirit of the present invention.

Each of the discs 10"""" include an upper housing member 12"""" and a lower housing member 14"""". The housing members 12"""", 14"""" each include a slot 35' within the housing member 12"""", 14"""". The slot 35' enables the bearing 23 to move freely or "float" within the slot 35' in response to movement of the housing 14. As shown in FIGS. 31, 33–34, and 38–39, the slot 35' can be formed in any shape that enables proper movement of the bearing 23, however, preferably the slot 35' is an open-ended u-shaped slot with a seat 39' and side walls 37'. The side walls 37' maintain the bearing 23 in proper alignment within the housing 12"""", 14"""". As disclosed above, the bearing 23 is capable of floating within the slot 35', thus enabling the bearing 23 to be mobile and free to move in any direction necessary to provide proper support for the housing 12"""", 14"""". The housing 12"""", 14"""" limits the motion of the bearing 23. The size of the housing 12"""", 14"""" and, more specifically, the slot 35' in which the bearing 23 is disposed limits the motion of the bearing 23. Further, bumpers 130, 132 can also be included in the slot 35' to further limit the motion of the bearing 23, provide dampening of the motion of the bearing 23 and prevent the bearing from being displaced from the housing 12"""", 14"""". The bumpers 130, 132 can be of any size sufficient to provide the necessary limitations on the bearing 23. For example, a single bumper can be used for both housings 12"""", 14"""". Alternatively, each housing 12"""", 14"""" can incorporate separate bumpers 130, 132. The bumpers 130, 132 are also useful for load sharing and thereby preventing the housing members 12"""", 14"""" from contacting one another. The bumpers of the present invention 130, 132 are shaped to conform to the shape of the slot 35'. In other words, the bumpers 130, 132 are shaped to precisely fit the slot 35' in which the bumpers 103, 132 are displaced. Preferably, the bumpers 130, 132 do not extend beyond the length of the housing 12"""", 14"""". The bumpers 130, 132 have walls 134, 136 respectively that engage the wall 37' of the slot 35'. This enables the bumpers 130, 132 to be maintained in alignment and prevents the bumpers 130, 132 from moving.

The upper housing 12"""" can either include a slot 35' identical to that of the lower housing 14"""" or can include a single piece having a matching bearing that complements that of the bearing 23. In other words, the upper housing 12"""" can either have a slot 35' that is identical to the shape of the slot 35' of the lower housing 14"""", such that the bearing 23 moves both in both housings 12"""", 14"""" equally or the upper housing 12"""" can be formed such that only a single piece is utilized and there is no movement within the top plate of the bearing 23.

The bearing 23' includes side arms 138, 140 that slidably engaged the wall 37' of the slot 35'. The bearing 23' is therefore held in position within the slot 35' via the side arms 138, 140 and the bumpers 130, 132.

Figure 32:
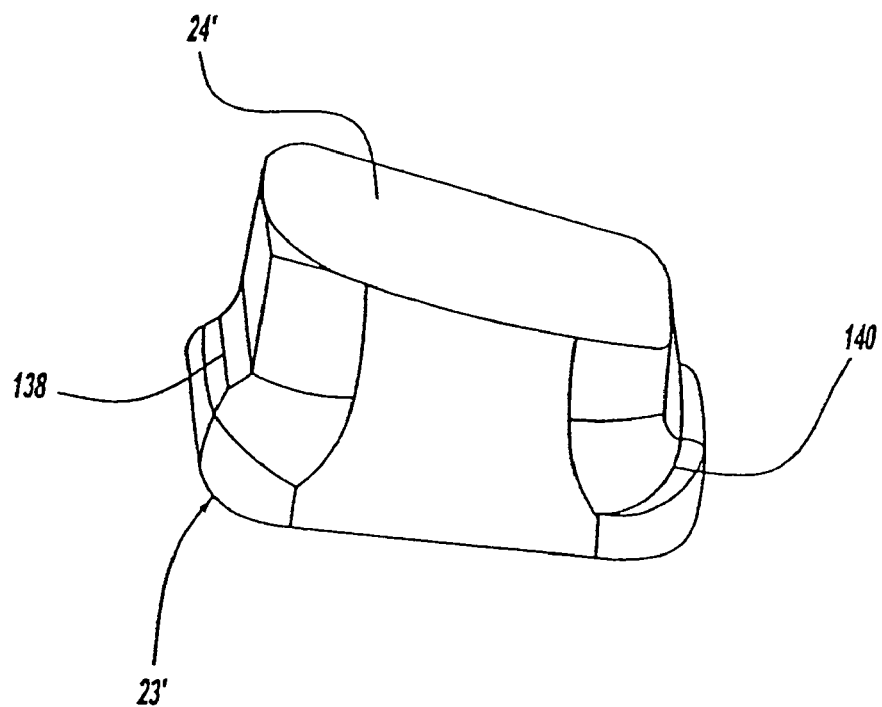
FIG. 32 is a side view of a third embodiment of the lower housing of the present invention.
Figure 33:
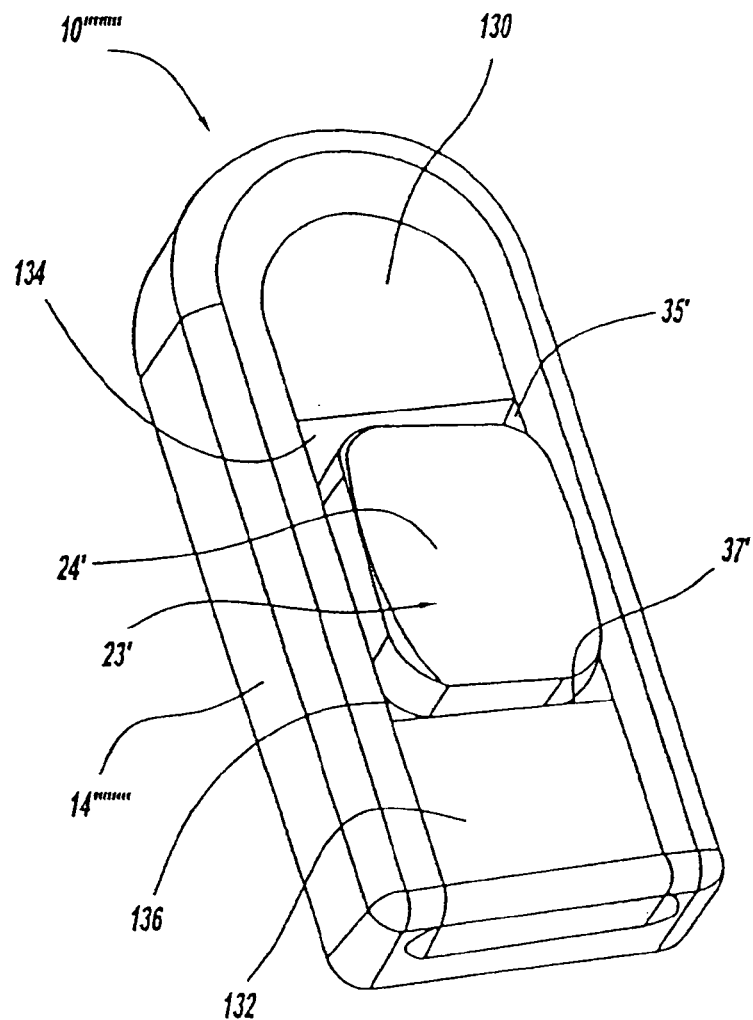
FIG. 33 is a perspective view of the third embodiment of the present invention wherein a spherical surface is incorporated on the bearing.
Figure 34:
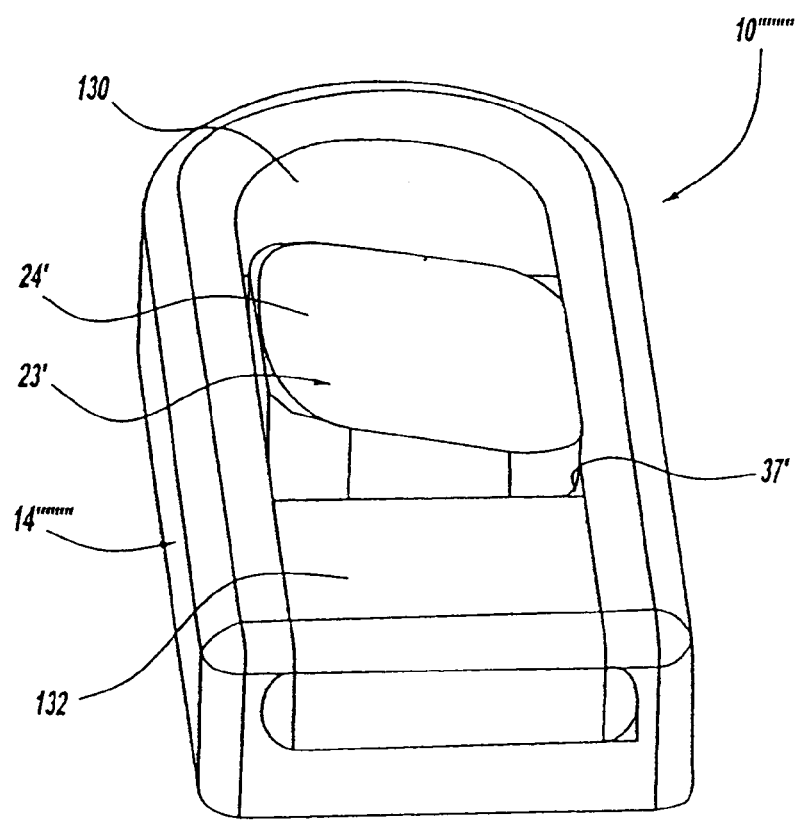
FIG. 34 is a perspective view of the third embodiment of the present invention wherein a spherical surface is incorporated on the bearing.
Figure 35:
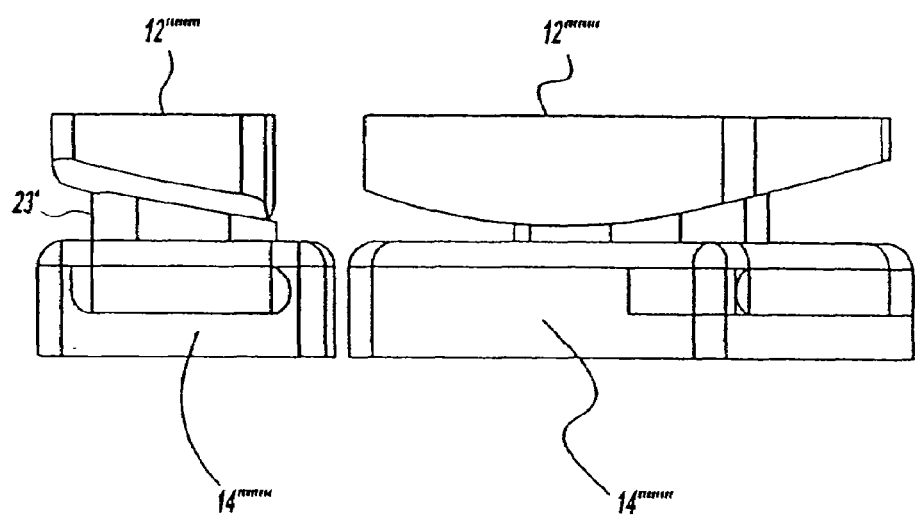
FIG. 35 is a side view of the third embodiment of the present invention.
Figure 36:
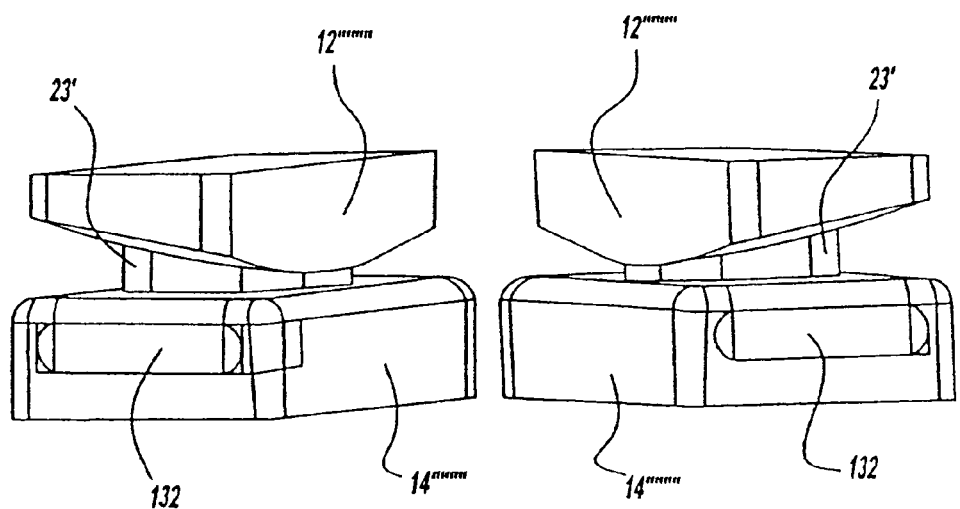
FIG. 36 is a side view of the third embodiment of the present invention.
Figure 37:
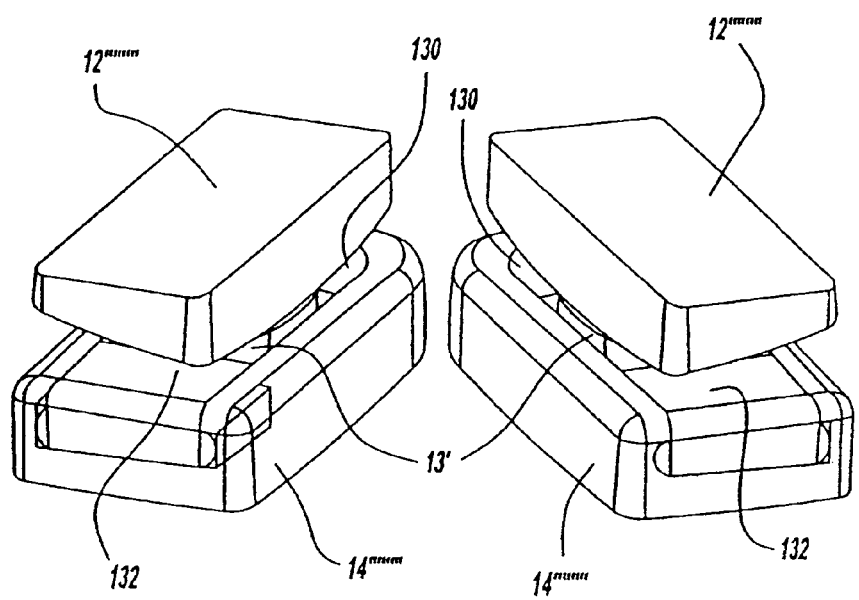
FIG. 37 is a side perspective view of an alternative embodiment of the present invention.
Figure 38:
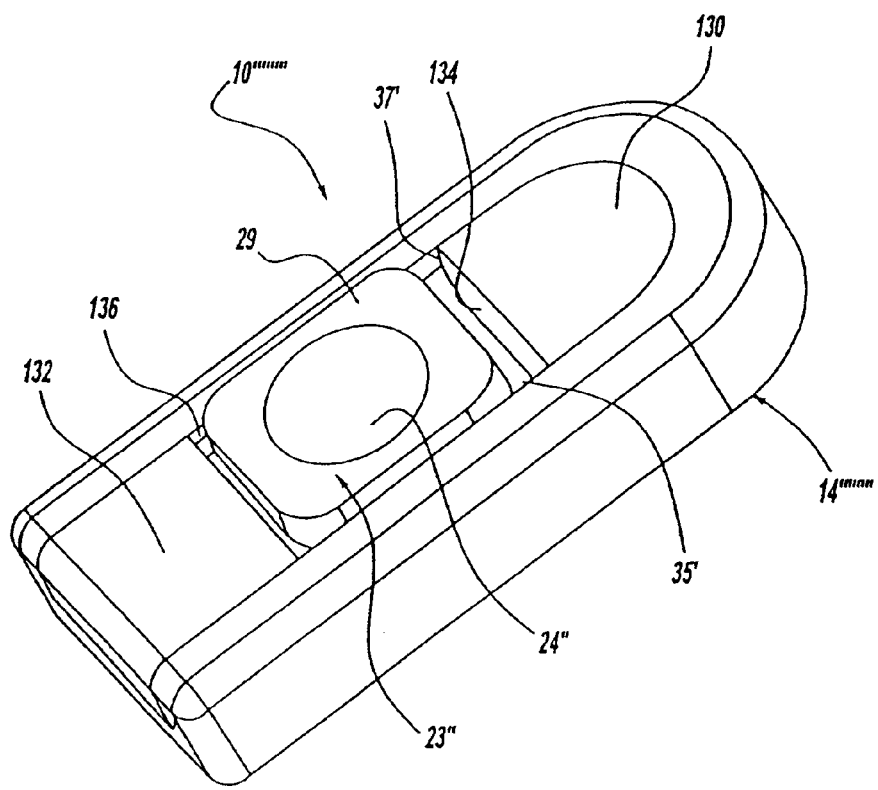
FIG. 38 is a perspective view of the base plate of the third embodiment of the present invention wherein the bearing is either convex or concave.
Figure 39:
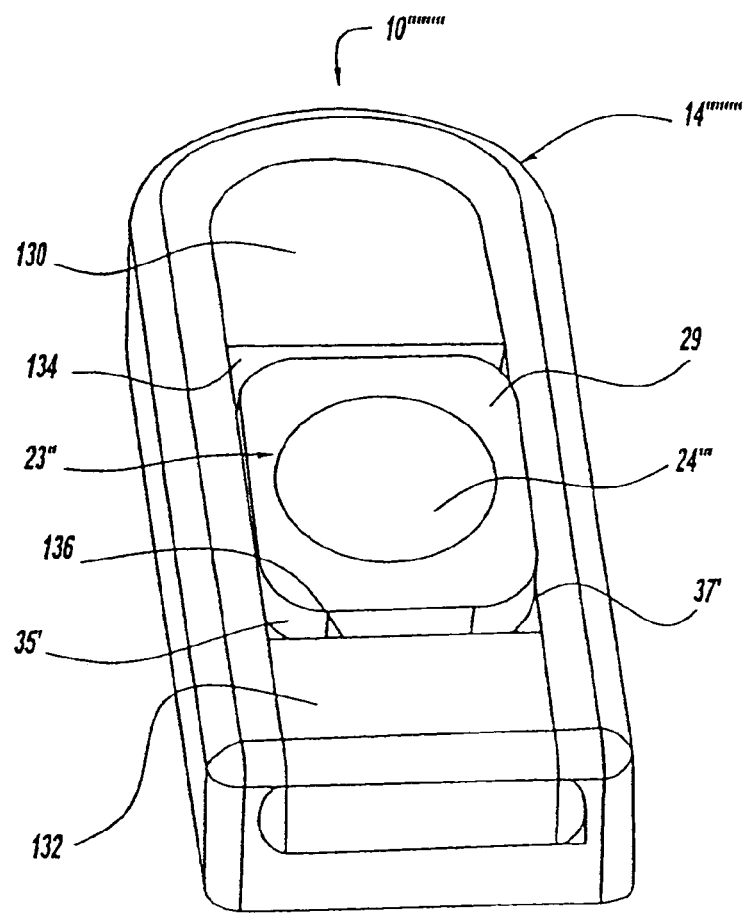
FIG. 39 is a perspective view of the base plate of the third embodiment of the present invention wherein the bearing is either convex or concave.
Figure 40:
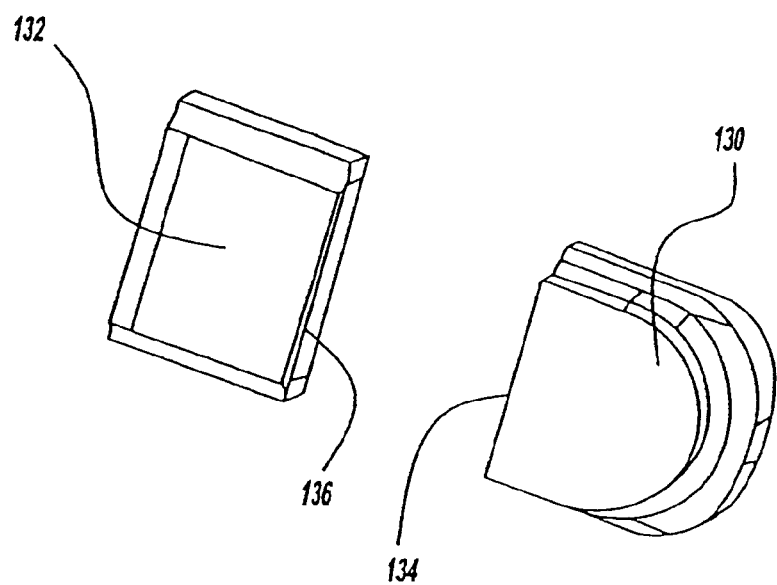
FIG. 40 is a top perspective view of the bumpers of the present invention.

The bearing 23 of the present invention can also have incorporated on the bearing surface 24 various shapes as shown in the figures. Specifically, FIG. 32 shows the bearing surface 24', wherein the surface 24' is a spherical surface.

The spherical surface 24' enables the center of rotation of the bearing 23' to exist at the center of the sphere. Therefore, the pair of discs 10'''''' functions as a single artificial disc with one center of rotation. Alternatively, the bearing 23 can have a surface that is either convex 24" or concave 24'''. This embodiment is specifically shown in FIGS. 9 and 10 wherein the center portion of the bearing 23' is either convex or concave and there is a flat portion 29 of the bearing 23'. When a convex or concave surface 24", 24''' respectively, is utilized, the rotation center is not in the center for side-to-side rotation. Thus, the assembly is somewhat resistant to side-to-side bending but is more easily aligned.

Figure 41A:
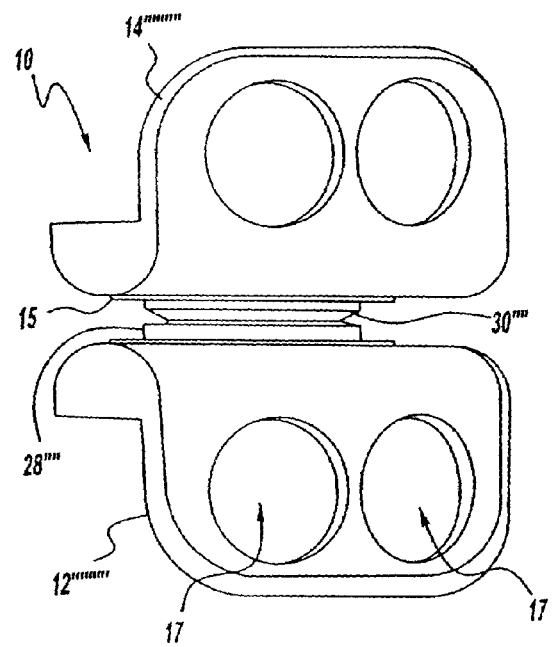
FIG. 41 is a perspective view of an embodiment of the housing members of the present invention, wherein the housing members include apertures for bone screws and a positioning ring.
Figure 41B:
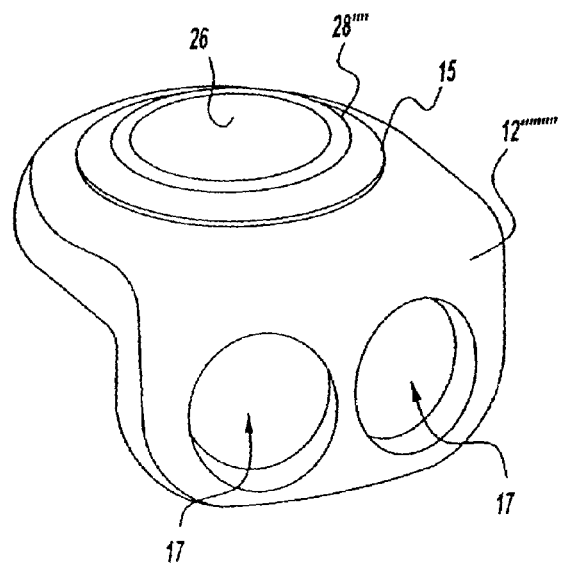
Figure 42A:
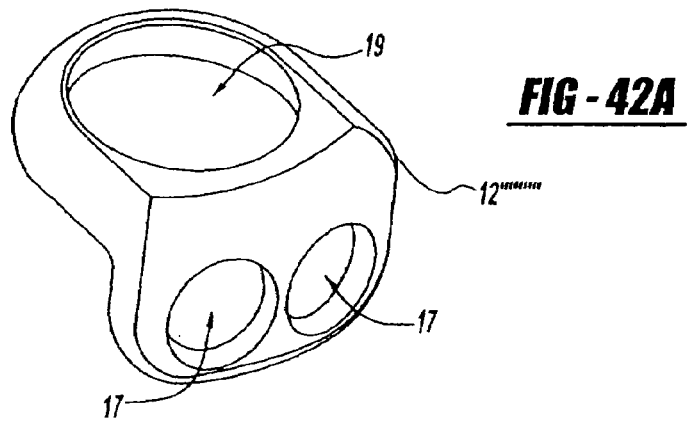
FIG. 42 is a perspective view of an embodiment of the housing members of the present invention, wherein a recess is shown for accommodating the positioning ring and bearing discs.
Figure 42B:
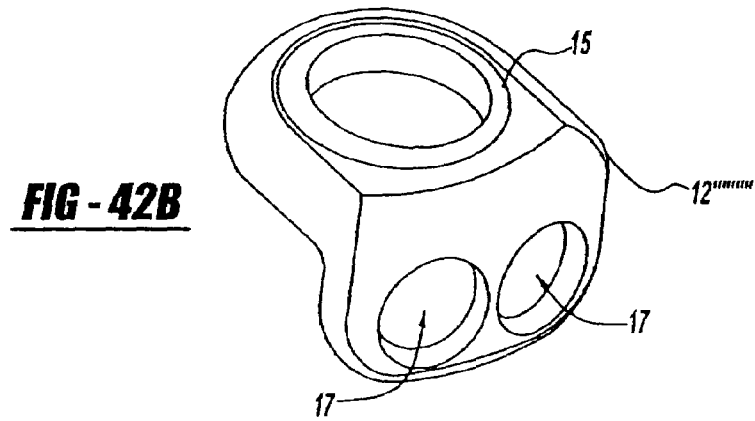
Figure 42C:
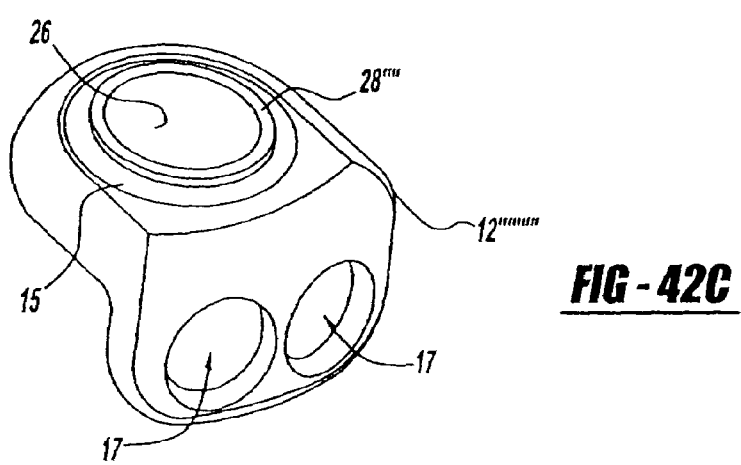
Figure 43:
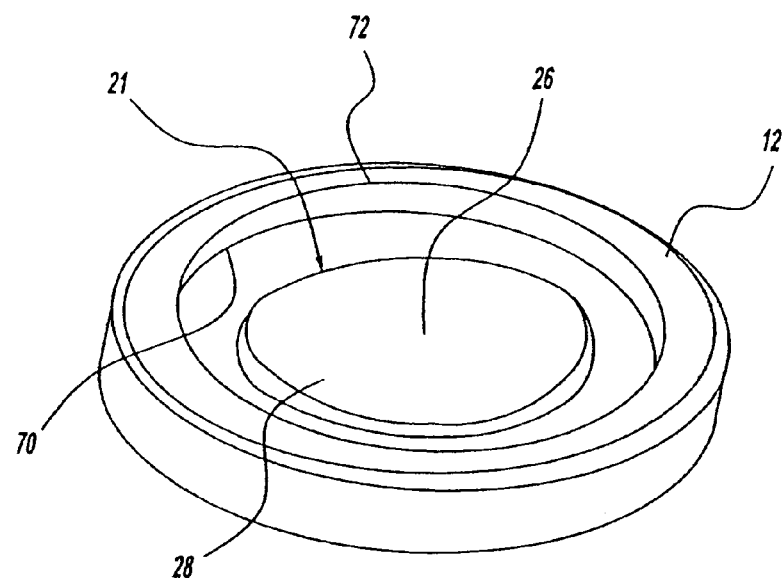
FIG. 43 is a perspective view of an embodiment of the housing member that is oval-shaped.

The housings 12'''''''', 14'''''''' can be inserted simultaneously without incorporating the floating bearing 23 initially. This enables the disc 10'''''''' to be inserted into the intervertebral space and once the disc 10'''''''' has been inserted, the bumpers 130, 132 and the bearing 23 can be slid into place within the slot 35'. In another embodiment of the present invention, the lower housing member 12'''''''' and the upper housing member 14'''''''' include a recess 52''' for seating a positioning ring 15, or spring mechanism 15, and bearing discs 28'''', 30'''' therein (See, FIGS. 41 and 42). Preferably, the recess 52''' includes a substantially arcuate peripheral undergroove 70" or wall 70" and a bottom surface 19 that can be super finished smooth. The recess 52''' accommodates the positioning ring 15 therein and the undergroove 70" secures the positioning ring 15. The undergroove 70" is defined by a lip portion 72". The housings 12'''''''', 14'''''''' include at least one aperture 17 for insertion of screws therein and to secure the housings 12'''''''', 14'''''''' to a vertebral body. The positioning ring 15 can be fixedly or removably attached to the housings 12'''''''', 14'''''''' Similarly, the bearing discs 28'''', 30'''' can be fixedly or removably attached to the housings 12'''''''', 14''''''''.

The positioning ring 15, or spring member 15, is elastomeric and can be made any material including, but not limited to, rubber, silicone, polyurethane, urethane composites, plastics, polymers, elastomers, and any other similar elastomeric material known to those of skill in the art. The positioning ring 15 is illustrated in detail in FIGS. 41–46. Preferably, the positioning ring 15 or spring member 15 is a substantially annular body including an axially extended bore therethrough defining a passageway. Although the positioning ring is circular in shape, any similar or appropriate design can be used such as an oval shape. Additionally, the substantially annular body has a seat extending radially inward towards the bore for seating therein the bearing discs 28, 30 and has an engaging member extending radially outward from the bore for engaging the recess 52 of the housing member 12, 14 and securing the positioning ring within the recess 52. Preferably, the engaging member can be any portion of the substantially annular body that radially extends from the bore. The engaging member includes, but is not limited to, a tapered edge, flange, and the like. The engaging member is shaped so as to be received by the recess and the recess securely engages the engaging member resulting in securing the positioning ring within the recess.

The purpose of the positioning ring 15 or spring member 15 is to absorb compressive loads between the bearing discs 28, 30 and the undergroove 70" or wall" of the recess of the housing member, while controlling motion and position of the bearing discs 28, 30. The positioning ring 15 cushions and provides bias to absorb compression and lateral forces, while acting as a spring to re-center the bearing discs 28, 30 after being displaced through vertebral function.

The bearing discs 28'''', 30'''' are situated within the opening of the positioning ring 15 or spring mechanism 15. The bearing discs 28'''', 30'''' can move within the positioning ring 15 and thus the housings 12'''''''', 14'''''''' therein. However, movement within the housings 12'''''''', 14'''''''' is semi-constrained by the positioning ring 15. The positioning ring acts as a spring to self-center the bearing discs 28'''', 30'''' and as a shock absorption member. As the bearing discs 28'''', 30'''' are free to float, the positioning ring 15 acts as a damper and self-centering spring. Therefore, the bearing can translate in any direction, while the positioning ring exerts a force to push the bearing back to center. The further the bearing moves, the more force the positioning ring 15 exerts. Any vertebral or spinal motion allows for load sharing and damping of forces to the spine. As a load is transmitted, the bearing discs 28'''', 30'''' move and the force is shared by the positioning ring 15 or spring mechanism 15.

Figure 44:
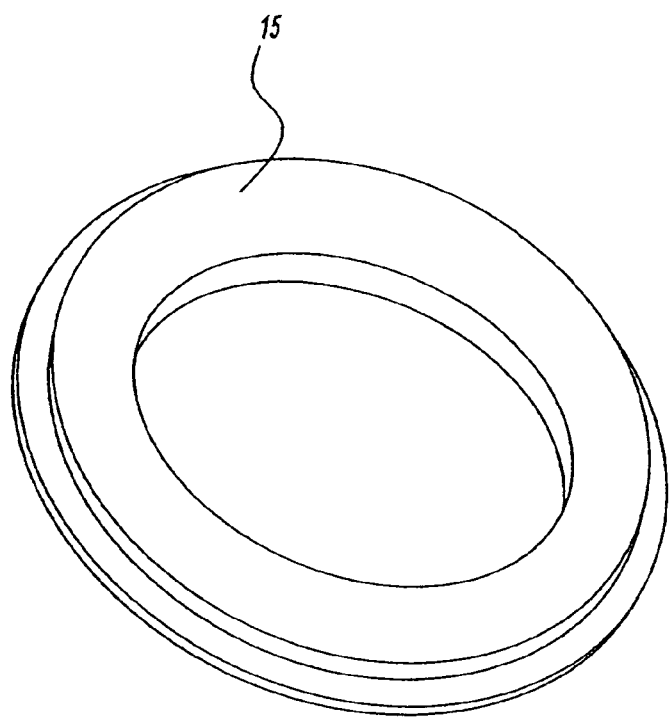
FIG. 44 is a perspective view of an oval-shaped positioning ring.
Figure 45:
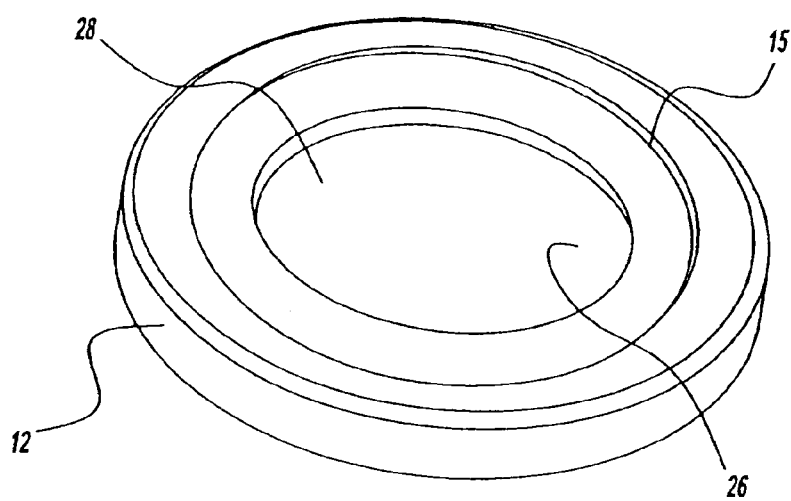
FIG. 45 is a perspective view of the oval-shaped positioning ring, bearing disc, and housing member.
Figure 46:
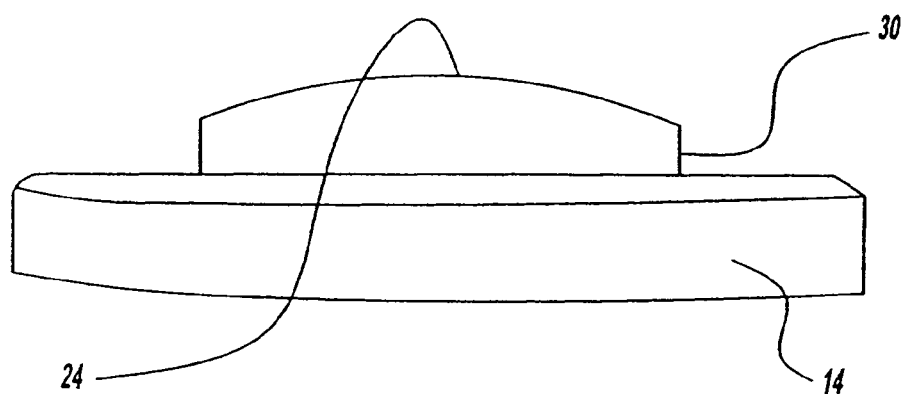
FIG. 46 is a side view of an upper housing member including a fixed bearing disc.
Figure 47:
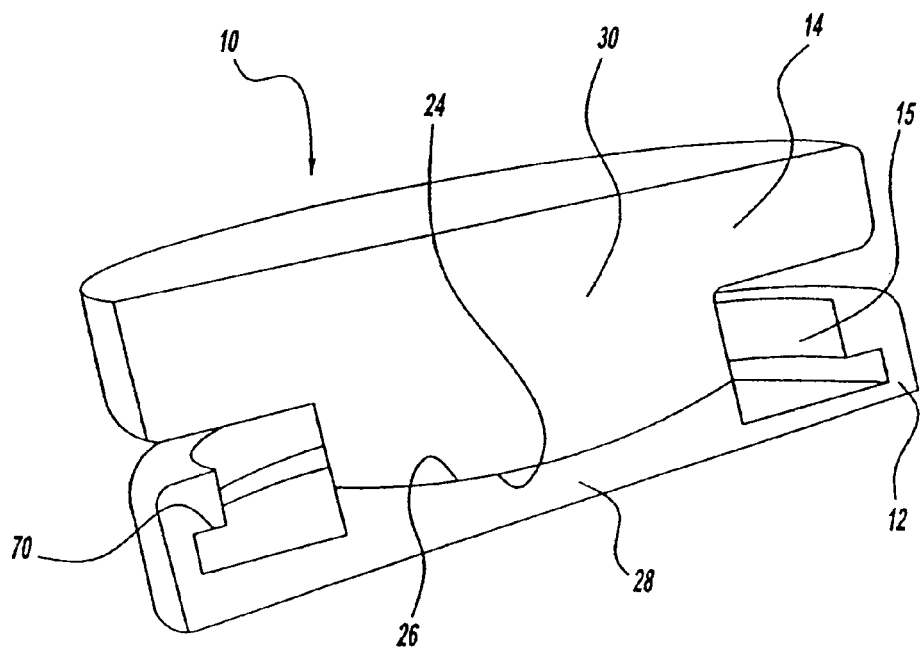
FIG. 47 is a cut away view of the disc of the present invention showing engagement of the bearing surfaces and engagement of the oval positioning ring, wherein the bearing disc is oval shaped and the recess on the housing member is oval-shaped.
Figure 48:
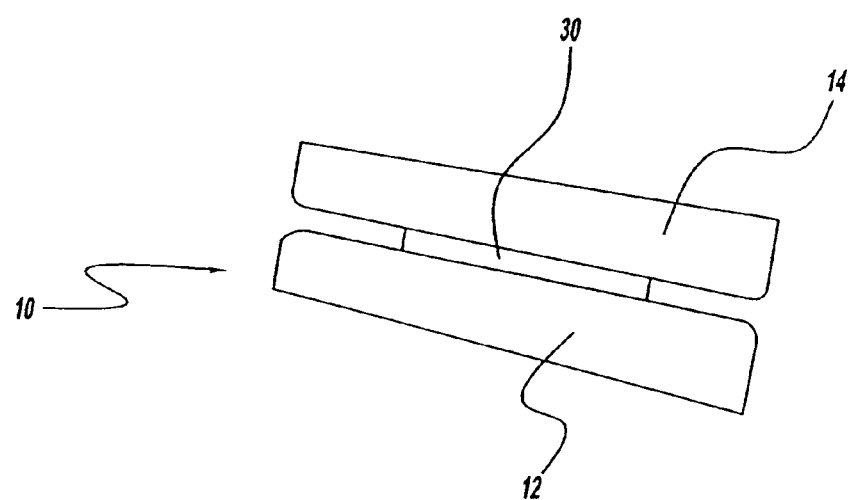
FIG. 48 is a perspective view of the disc assembly of the present invention.

In another embodiment of the present invention, the bearing discs 28'''', 30'''' along with the positioning ring 15' are oval shaped. Additionally, the recess 52'''' located on each housing member 12'''''''', 14 '''''''' is oval-shaped, while the housing members 12, 14 can also be oval shaped, circular, or any other suitable shape known to those of skill in the art. The recess 52'''' accommodates the positioning ring 15' therein and an undergroove 70''' secures the positioning ring 15'. The undergroove 70''' is defined by a lip portion 72'''As shown in FIGS. 43-48, the bearing discs 28'''', 30'''' can be fixed within the oval recess 52''' or the bearing discs 28'''', 30'''' can be floating (i.e., mobile bearing discs) within the oval recess 52''' of the housing members 12'''''''', 14''''''''. The bearing discs 28'''', 30'''' have oval circumferential exterior sides 21 and a spherical surface machined into the bearing surface 24, 26. FIG. 44 illustrates the approximate shape of the positioning ring 15'. FIG. 45 shows the positioning ring 15' in place within the recess 52'''' and illustrates the oval shape in greater detail. FIG. 46 illustrates an upper housing member 14'''''''', wherein the bearing disc 30'''' is fixed onto the upper housing member 14''''''''. The exterior circumference of the bearing discs is oval, with the bearing surface 24, 26 being spherical.

Under rotational loads, positioning ring 15' engages the oval circumferential exterior sides 21 of the bearing discs 28'''', 30'''' and the undergroove 70''' of the recess 52'''' of the housing members 12'''''''', 14''''''''. The greater the rotation, the more compressive force is exerted against the positioning ring 15'. Therefore, the disc 10 acts similar to a normal anatomic disc, whereby the annulus allows motion, but also provides constraint of excessive motion. With such a rotation, the positioning ring 15' acts as a spring counteracting the rotational forces to allow rotation, while preventing excess rotation therefrom. The positioning ring 15' can be changed in durometer to create more motion or less motion by altering the effective spring rate of the material. Thus, patient specific positioning rings 15' can be chosen based on patient requirements. In cases where facet joints are deteriorated, the disc 10 can compensate by using a higher durometer positioning ring 15' and allowing the surgeon full optimization at the time of surgery.

Under translation loads, the positioning ring 15' acts as a spring to resist excessive motion, while acting as a spring to self-center the disc construct. As shown in Figures, the oval aspect allows the necessary engagement area to permit the combination of benefits. Also, by using such an oval surface, the positioning ring 15' remains in compression at all times, allowing maximum benefit and performance from various polymers. To one skilled in the art, the oval recess 52'''' could be any elongated surface that effectively provides some moment arm to exert force on the positioning ring 15'.

Various methods can be utilized for insertion of the present invention in situ. For example, an assembled device 10 as shown in FIG. 1, can be disposed between the intervertebral spaces during surgery, after calculation of space, depth, and height. Alternatively, opposing housing members 12, 14 can be disposed between the intervertebral spaces and pads 31 and disc members 24, 26 can be tested in situ prior to fixation thereof to allow for custom sizing. Accordingly, the present invention broadly provides a method of assembling an artificial intervertebral disc 10 in vivo by inserting upper and lower housing members 12, 14 into an intervertebral space and disposing cushioning pads 31 between the inner surfaces 16, 18 of the housing members 12, 14, thereby placing the pads in compression. The pair of disc members 28, 30 is inserted between the inner surfaces of the plates 16, 18. The disc members 28, 30 have abutting low friction surfaces 24, 26 therebetween. The disc members 28, 30 are surrounded by the pads 31, whereby the disc members 28, 30 and pads 31 are under compressive forces and share such compressive forces. This step of the bearing surfaces 24, 26 and shock absorbing pads 31 sharing absorption of the compressive forces and limiting the relative movement of the housing members 12, 14 is an advantage not found in the prior art.

One use of the bearing of the present invention is in an artificial intervertebral disc for replacement of a damaged disc in the spine. The artificial disc 10 of the present application includes a mobile bearing 23 that allows for the bearing 23 to move to adjust and compensate for vertebral disc motion. By permitting the bearing to self-adjust, the bearing 23 can more freely move under translation loading conditions while maximizing the contact area of the upper and lower bearing surfaces 20, 24.

In applications such as the lumbar spine, the disc upper member and lower member are angled relative to each other to maintain spinal curvature. The load distributing damper and cushioning pads are always under some load when the spine is moving, although they can be adjusted for a neutral no load situation when the spine is not moving.

The load distributing damper and cushioning pads also create an elastic means of self-centering the disc construct. Deflection of rotation of the disc forces the pads to act in such a way as to counter the force, thus allowing a unique self-centering capability. In an ideal situation where the patient's facets are uncompromised and ligamental balance is intact, this is not necessary. However, ligamental balance and damaged facets would normally make an artificial disc questionable at best with the current art. In such cases, having the ability to self-centering center and restrict motion (the pads are elastic and thus restrict motion by stretching and returning to rest), the possibilities of extending indications to patients currently considered outside the scope of artificial disc technology is highly advantageous. In a floating bearing design, the ability to self-center mixed with the dampening abilities of the pads creates an ideal system for an artificial disc.

The pads can also be adjusted according to patient and surgeon requirements. In such cases where range of motion needs to be restricted due to compromised facets, a harder, less elastic pad can be inserted. Since a less elastic pad moves and stretches less, the disc is automatically restricted in motion. This method of adjusting pads can be done interoperatively to compensate for surgical and patient conditions.

Figure 49:
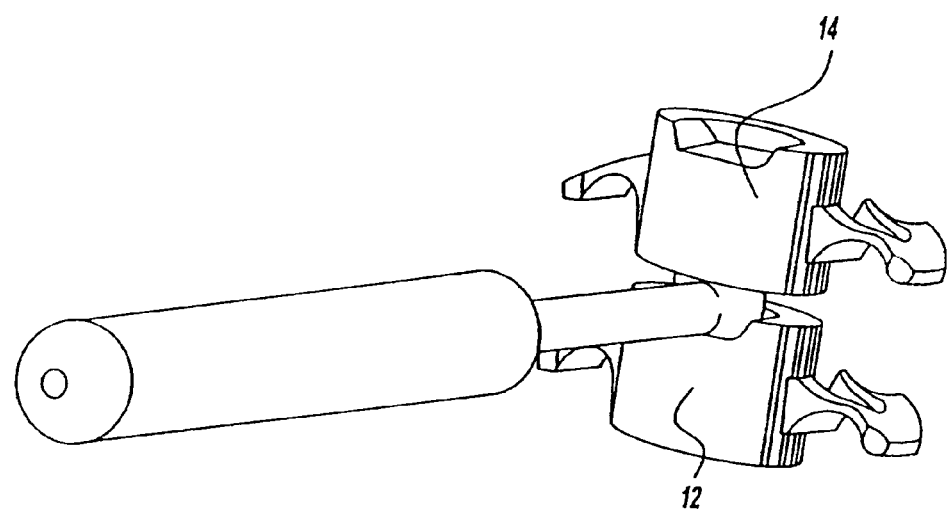
FIG. 49 illustrates the insertion of a trial into the disc space.
Figure 50:
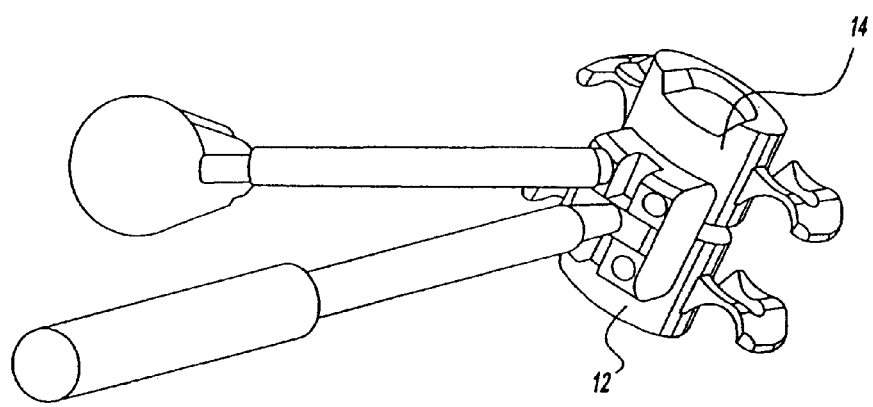
FIG. 50 illustrates a drill guide for use in drilling pilot holes at a guide plate locations.
Figure 51:
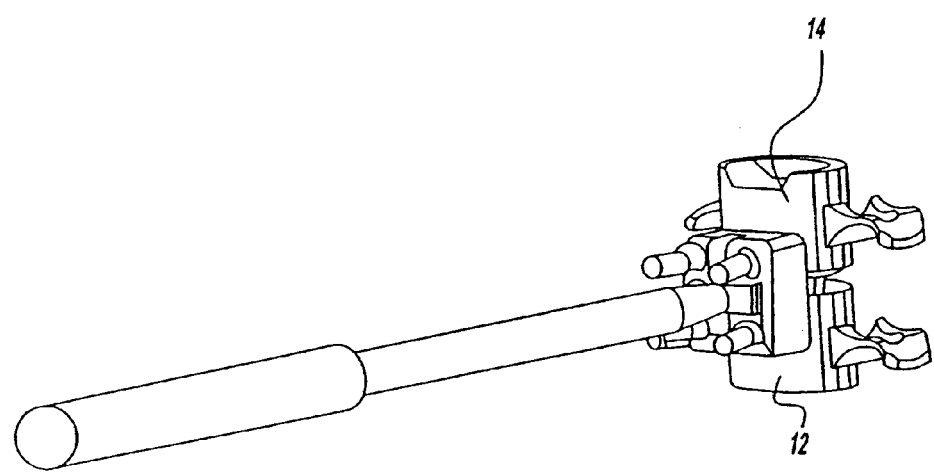
FIG. 51 illustrates securing the guide plate with self-tapping guide plate screws.
Figure 52:
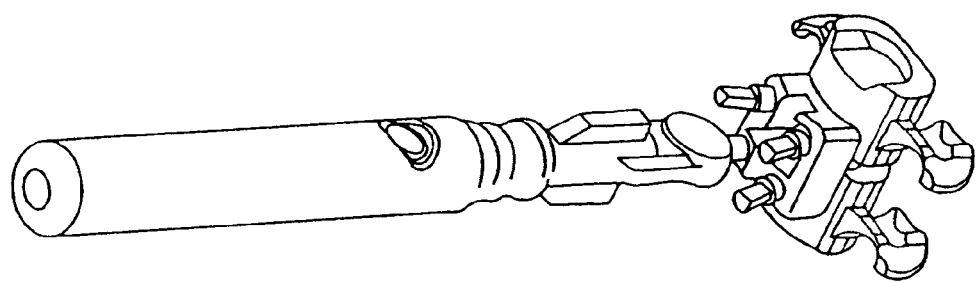
FIG. 52 illustrates inserting reaming discs matching the trial number into the disc assembly.
Figure 53:
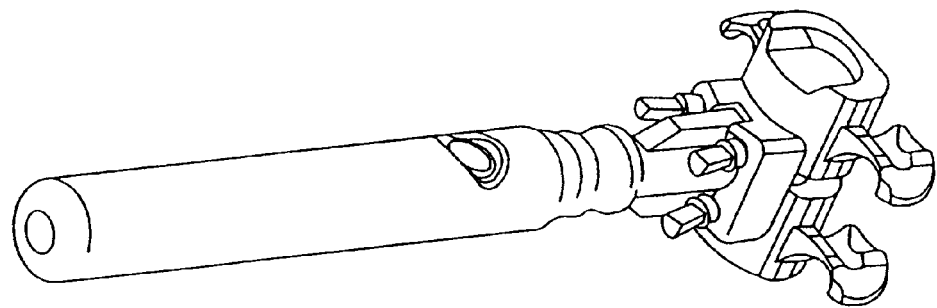
FIG. 53 illustrates engagement of the trial with the disc assembly.
Figure 54A:
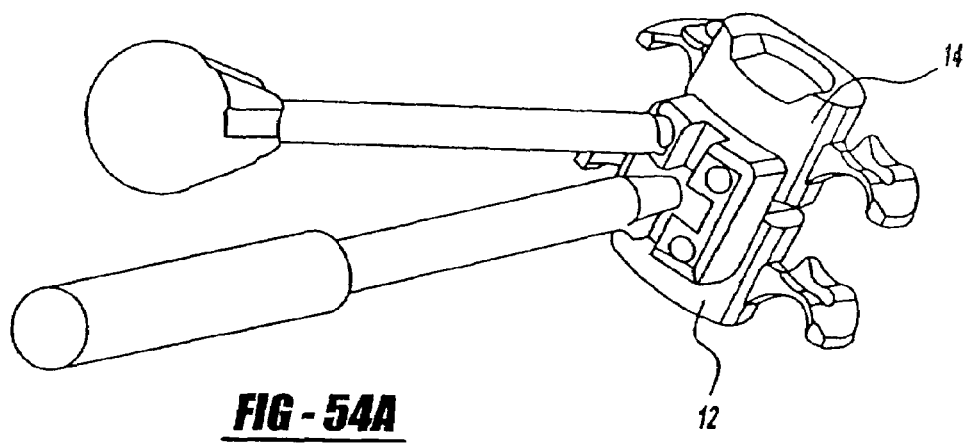
FIG. 54 illustrates removal of guide plate screws and guide plate.
Figure 54B:
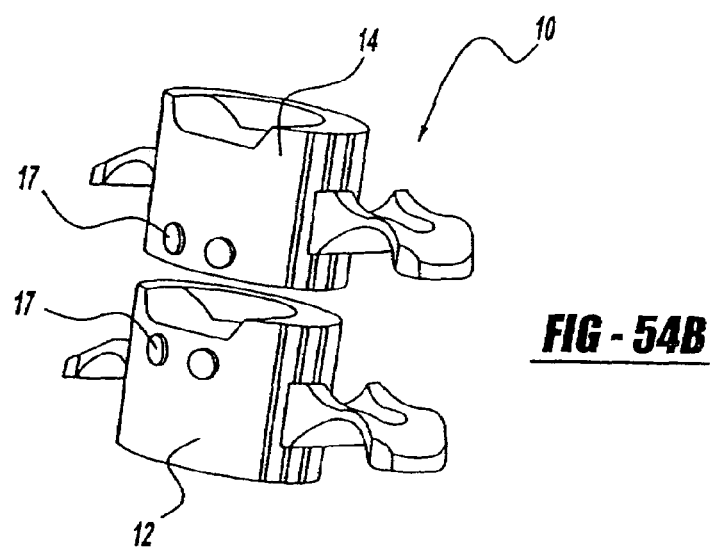
Figure 55:
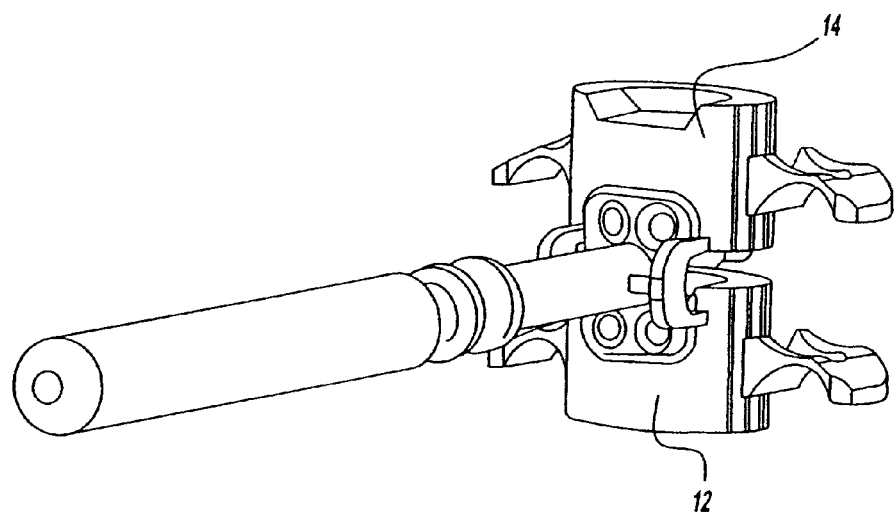
FIG. 55 illustrates insertion of disc holder with holes in plate.
Figure 56:
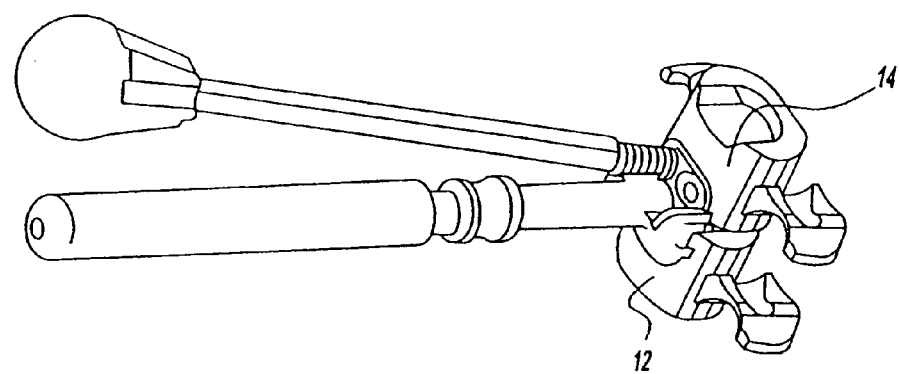
FIG. 56 illustrates insertion of screws into threaded holes to secure disc to the vertebral bodies.
Figure 57:
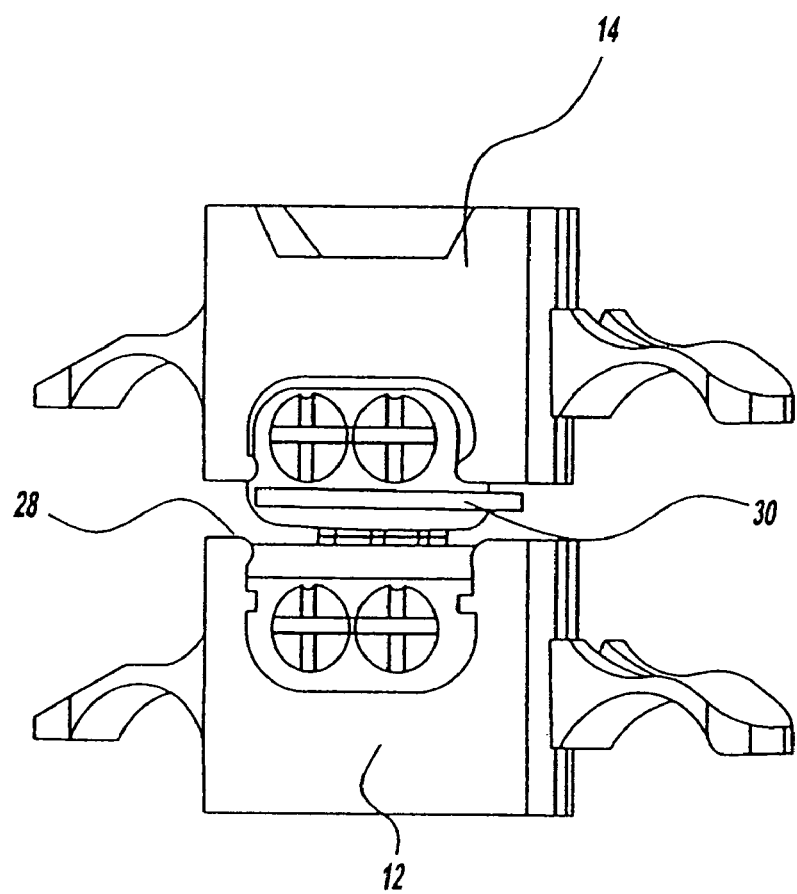
FIG. 57 illustrates attached disc assembly.

As described above, any of the above embodiments can be used in a cervical disc surgical procedure. With regard to the embodiment of the housing members 12, 14 illustrated in FIGS. 41 and 42, the general procedure begins with the removal of the damaged disc (FIGS. 49–57 illustrate the procedure). Then, a trial handle is attached to the trial and the trial is inserted into the disc space (FIG. 49). The trial is adjusted until the disc height is approximately restored, while being careful not to overstretch the ligaments. Using a drill guide, pilot holes are drilled at the four guide plate hole locations (FIG. 50). The guide plate is secured with self-tapping guide plate screws (FIG. 51). Using the end plate preparation instrument, reaming disks are inserted to match the trial number. The depth of the instrument on the dial to the matching number must then be set. Once set, the instrument is advanced into the disc space with the button engaged (FIG. 52). The fins on the instrument remain engaged in the slot on the guide plate for stability. Once maximum depth is reached, the end plate preparation instrument is removed (FIG. 53). The guide plate screws and guide plate are then removed (FIG. 54). The disc holder with holes in plate aligned with holes in the vertebrae is inserted until fully seated (FIG. 55). Screws are then inserted into threaded holes to secure disc to the vertebral bodies (FIG. 56). Finally, the disc inserter is removed (FIG. 57).

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. An artificial intervertebral disc comprising:
   housing members having spaced inner surfaces, at least one inner surface having a recess and a peripheral groove extending outwardly from the recess;
   a bearing operatively disposed between the inner surfaces for moving relative to the housing members to adjust and compensate for vertebral disc motion, the bearing comprising a first bearing disc and a second bearing disc slidably engaging the first bearing disc along a bearing surface; and
   a resilient flexible positioning ring surrounding the bearing for absorbing shock and centering the bearing in response to movement, the positioning ring having a body portion and an engaging member extending radially outwardly from the body portion into the peripheral groove to secure the positioning ring in at least one of the housing members.

2. The disc according to claim 1, wherein the positioning ring forms an axial bore, and the first and second bearing discs engage one another within the axial bore.

3. The disc according to claim 1, wherein the engaging member includes a generally circular flange extending outwardly from the perimeter of the positioning ring.

4. The disc according to claim 3, wherein the peripheral groove is generally circular, and the radius of the flange and radius of the groove are substantially identical.

5. The disc according to claim 1 wherein the housing members include an outer surface having a coating thereon selected from the group consisting essentially of TiN (Titanium Nitride), diamond, diamond-like materials, synthetic carbon-based materials, and chromium-based materials.

6. The disc according to claim 1, wherein the bearing is constructed from a composition selected from the group consisting essentially of metals, ceramics, and plastics.

7. The disc according to claim 1, wherein the positioning ring is made of materials selected from the group consisting essentially of rubber, silicone, polyurethane, urethane composites, plastics, polymers and elastomers.

8. The disc according to claim 1, wherein the housing members include at least one aperture for accommodating at least one bone screw.

9. An artificial intervertebral disc comprising:
housing members having spaced inner surfaces, at least one inner surface having a recess and an annular lip extending radially inwardly above the recess;
a bearing operatively disposed between the inner surfaces for moving relative to the housing members to adjust and compensate for vertebral disc motion, the bearing comprising a first bearing disc and a second bearing disc slidably engaging the first bearing disc along a bearing surface; and
a resilient flexible positioning ring surrounding the bearing for absorbing shock and centering the bearing in response to movement, the positioning ring having a body portion and an engaging member extending radially outwardly from the body portion into engagement with the annular lip to fix the axial position of the positioning ring relative to at least one of the housing members.

10. The disc according to claim 9, wherein the positioning ring forms an axial bore, and the first and second bearing discs engage one another within the axial bore.

11. The disc according to claim 9, wherein the engaging member includes a generally circular flange extending outwardly from the perimeter of the positioning ring.

12. The disc according to claim 11, wherein the peripheral groove is generally circular, and the radius of curvature of the flange and groove are substantially identical.

13. The disc according to claim 12, wherein the housing members include an outer surface having a coating thereon selected from the group consisting essentially of TiN (Titanium Nitride), diamond, diamond-like materials, synthetic carbon-based materials, and chromium-based materials.

14. The disc according to claim 9, wherein the bearing is constructed from a composition selected from the group consisting essentially of metals, ceramics, and plastics.

15. The disc according to claim 9, wherein the positioning ring is made of materials selected from the group consisting essentially of rubber, silicone, polyurethane, urethane composites, plastics, polymers and elastomers.

16. The disc according to claim 9, wherein the housing members include at least one aperture for accommodating at least one bone screw.

* * * * *